(12) United States Patent
Aljuri et al.

(10) Patent No.: US 8,454,527 B2
(45) Date of Patent: Jun. 4, 2013

(54) MINIMALLY INVASIVE DETERMINATION OF COLLATERAL VENTILATION IN LUNGS

(75) Inventors: Nikolai Aljuri, Hillsborough, CA (US);
Anthony Wondka, Thousand Oaks, CA (US); George Surjan, San Jose, CA (US); Kirk Davis, Los Gatos, CA (US); Peter Soltesz, San Jose, CA (US); Rodney C. Perkins, Woodside, CA (US)

(73) Assignee: Pulmonx Corporation, Redwood City, CA (US)

( * ) Notice: Subject to any disclaimer, the term of this patent is extended or adjusted under 35 U.S.C. 154(b) by 115 days.

(21) Appl. No.: 12/972,225

(22) Filed: Dec. 17, 2010

(65) Prior Publication Data

US 2011/0087122 A1   Apr. 14, 2011

Related U.S. Application Data

(63) Continuation of application No. 11/296,951, filed on Dec. 7, 2005, now Pat. No. 7,883,471, which is a continuation-in-part of application No. 10/241,733, filed on Sep. 10, 2002.

(60) Provisional application No. 60/699,289, filed on Jul. 13, 2005, provisional application No. 60/696,940, filed on Jul. 5, 2005, provisional application No. 60/645,711, filed on Jan. 20, 2005, provisional application No. 60/318,539, filed on Sep. 10, 2001.

(51) Int. Cl.
*A61B 5/08* (2006.01)

(52) U.S. Cl.
USPC .......................................... 600/532; 800/538

(58) Field of Classification Search
USPC .................................... 600/529–543; 73/23.3
See application file for complete search history.

(56) References Cited

U.S. PATENT DOCUMENTS

| 3,322,126 | A | 5/1967 | Rusch et al. |
| 3,459,331 | A | 8/1969 | Hogg |
| 3,474,940 | A | 10/1969 | Hogg |

(Continued)

FOREIGN PATENT DOCUMENTS

| EP | 0 692 273 | 1/1996 |
| EP | 1 078 601 | 8/2000 |

(Continued)

OTHER PUBLICATIONS

European search report dated Nov. 16, 2009 for EP Application No. 06717427.6.

(Continued)

*Primary Examiner* — Navin Natnithithadha
(74) *Attorney, Agent, or Firm* — Wilson, Sonsini, Goodrich & Rosati

(57) ABSTRACT

Minimally invasive methods, systems and devices are provided for qualitatively and quantitatively assessing collateral ventilation in the lungs. In particular, collateral ventilation of a target compartment within a lung of a patient is assessed by advancement of a catheter through the tracheobronchial tree to a feeding bronchus of the target compartment. The feeding bronchus is occluded by the catheter and a variety of measurements are taken with the use of the catheter in a manner which is of low risk to the patient. Examples of such measurements include but are not limited to flow rate, volume and pressure. These measurements are used to determine the presence of collateral ventilation and to quantify such collateral ventilation.

16 Claims, 31 Drawing Sheets

U.S. PATENT DOCUMENTS

| | | | |
|---|---|---|---|
| 3,498,286 A | 3/1970 | Polanyi et al. | |
| 3,669,098 A | 6/1972 | Takahashi | |
| 3,677,262 A | 7/1972 | Zukowski | |
| 3,776,222 A | 12/1973 | Smiddy | |
| 3,866,599 A | 2/1975 | Johnson | |
| 3,913,568 A | 10/1975 | Carpenter | |
| 4,031,885 A | 6/1977 | Davis et al. | |
| 4,034,743 A * | 7/1977 | Greenwood et al. | 600/538 |
| 4,041,936 A | 8/1977 | Carden | |
| 4,327,720 A | 5/1982 | Bronson et al. | |
| 4,327,721 A | 5/1982 | Goldin et al. | |
| 4,413,632 A | 11/1983 | Schlessinger et al. | |
| 4,453,545 A | 6/1984 | Inoue | |
| 4,468,216 A | 8/1984 | Muto | |
| 4,567,882 A | 2/1986 | Heller | |
| 4,716,896 A | 1/1988 | Ackerman | |
| 4,742,819 A | 5/1988 | George | |
| 4,784,133 A | 11/1988 | Macklin | |
| 4,796,639 A | 1/1989 | Snow et al. | |
| 4,819,664 A | 4/1989 | Nazari | |
| 4,846,153 A | 7/1989 | Berci | |
| 4,850,371 A | 7/1989 | Broadhurst et al. | |
| 4,862,874 A | 9/1989 | Kellner | |
| 4,896,941 A | 1/1990 | Hayashi et al. | |
| 4,949,716 A | 8/1990 | Chenoweth | |
| 4,955,375 A | 9/1990 | Martinez | |
| 4,958,932 A | 9/1990 | Kegelman et al. | |
| 4,961,738 A | 10/1990 | Mackin | |
| 4,972,842 A | 11/1990 | Korten et al. | |
| 4,976,710 A | 12/1990 | Mackin | |
| 5,056,529 A | 10/1991 | de Groot | |
| 5,143,062 A | 9/1992 | Peckham | |
| 5,146,916 A | 9/1992 | Catalani | |
| 5,285,778 A | 2/1994 | Mackin | |
| 5,305,740 A * | 4/1994 | Kolobow | 128/207.14 |
| 5,309,903 A | 5/1994 | Long | |
| 5,331,947 A | 7/1994 | Shturman | |
| 5,361,753 A | 11/1994 | Pothmann et al. | |
| 5,429,123 A * | 7/1995 | Shaffer et al. | 128/204.23 |
| 5,429,127 A * | 7/1995 | Kolobow | 128/207.14 |
| 5,447,165 A | 9/1995 | Gustafss | |
| 5,477,851 A | 12/1995 | Callaghan et al. | |
| 5,499,625 A | 3/1996 | Frass et al. | |
| 5,598,840 A | 2/1997 | Iund et al. | |
| 5,615,669 A * | 4/1997 | Olsson et al. | 128/203.12 |
| 5,642,730 A | 7/1997 | Baran | |
| 5,645,519 A | 7/1997 | Lee et al. | |
| 5,653,231 A | 8/1997 | Bell | |
| 5,660,175 A | 8/1997 | Dayal | |
| 5,682,880 A | 11/1997 | Brain | |
| 5,692,497 A | 12/1997 | Schnitzer et al. | |
| 5,707,352 A | 1/1998 | Sekins et al. | |
| 5,752,921 A | 5/1998 | Orr | |
| 5,957,128 A * | 9/1999 | Hecker et al. | 128/204.22 |
| 5,957,919 A | 9/1999 | Laufer | |
| 5,972,026 A | 10/1999 | Laufer et al. | |
| 6,068,602 A | 5/2000 | Tham et al. | |
| 6,083,255 A | 7/2000 | Laufer et al. | |
| 6,174,323 B1 | 1/2001 | Biggs et al. | |
| 6,283,988 B1 | 9/2001 | Laufer et al. | |
| 6,287,290 B1 | 9/2001 | Perkins et al. | |
| 6,390,988 B1 * | 5/2002 | Robinson | 600/531 |
| 6,398,775 B1 * | 6/2002 | Perkins et al. | 604/514 |
| 6,527,761 B1 | 3/2003 | Buch et al. | |
| 6,585,639 B1 | 7/2003 | Kotmel et al. | |
| 6,629,951 B2 | 10/2003 | Laufer et al. | |
| 6,659,961 B2 * | 12/2003 | Robinson | 600/531 |
| 6,692,494 B1 | 2/2004 | Cooper et al. | |
| 6,709,401 B2 | 3/2004 | Soltesz et al. | |
| 6,712,812 B2 | 3/2004 | Roschak et al. | |
| 6,749,606 B2 | 6/2004 | Keast et al. | |
| 6,878,141 B1 * | 4/2005 | Perkins et al. | 604/516 |
| 6,886,558 B2 | 5/2005 | Tanaka | |
| 6,997,189 B2 | 2/2006 | Biggs et al. | |
| 7,022,088 B2 | 4/2006 | Keast et al. | |
| 7,086,398 B2 | 8/2006 | Tanaka | |
| 7,141,046 B2 * | 11/2006 | Perkins et al. | 604/514 |
| 7,175,644 B2 | 2/2007 | Cooper et al. | |
| 7,186,259 B2 * | 3/2007 | Perkins et al. | 606/108 |
| 7,252,086 B2 | 8/2007 | Tanaka | |
| 7,377,278 B2 | 5/2008 | Tanaka | |
| 7,406,963 B2 | 8/2008 | Chang et al. | |
| 7,412,977 B2 * | 8/2008 | Fields et al. | 128/200.24 |
| 7,458,963 B2 * | 12/2008 | Perkins et al. | 604/514 |
| 7,473,219 B1 | 1/2009 | Glenn | |
| 7,530,353 B2 * | 5/2009 | Choncholas et al. | 128/204.18 |
| 7,588,033 B2 | 9/2009 | Wondka | |
| 7,686,013 B2 | 3/2010 | Chang et al. | |
| 7,726,305 B2 | 6/2010 | Chang et al. | |
| 7,766,895 B2 * | 8/2010 | Soltesz et al. | 604/516 |
| 7,883,471 B2 * | 2/2011 | Aljuri et al. | 600/529 |
| 8,104,473 B2 | 1/2012 | Tanaka | |
| 8,177,769 B2 * | 5/2012 | Perkins et al. | 604/516 |
| 8,220,460 B2 | 7/2012 | Tanaka | |
| 2002/0049370 A1 | 4/2002 | Laufer et al. | |
| 2002/0087153 A1 | 7/2002 | Roschak et al. | |
| 2002/0104542 A1 | 8/2002 | Castor et al. | |
| 2002/0111619 A1 | 8/2002 | Keast et al. | |
| 2002/0111620 A1 | 8/2002 | Cooper et al. | |
| 2003/0051733 A1 | 3/2003 | Kotmel et al. | |
| 2003/0228344 A1 | 12/2003 | Fields et al. | |
| 2004/0073201 A1 | 4/2004 | Cooper et al. | |
| 2004/0220556 A1 | 11/2004 | Cooper et al. | |
| 2004/0243016 A1 | 12/2004 | Sanderson et al. | |
| 2005/0005936 A1 | 1/2005 | David | |
| 2005/0016530 A1 | 1/2005 | McCutcheon et al. | |
| 2006/0264772 A1 | 11/2006 | Aljuri et al. | |
| 2007/0142742 A1 | 6/2007 | Aljuri et al. | |
| 2007/0247335 A1 | 10/2007 | Schiek et al. | |
| 2011/0270116 A1 | 11/2011 | Freitag et al. | |

FOREIGN PATENT DOCUMENTS

| | | |
|---|---|---|
| WO | WO 92/10971 | 7/1992 |
| WO | WO 95/33506 | 12/1995 |
| WO | WO 98/44854 | 10/1998 |
| WO | WO 99/01076 A1 | 1/1999 |
| WO | WO 99/20332 A1 | 4/1999 |
| WO | WO 99/34741 A1 | 7/1999 |
| WO | WO 99/64109 | 12/1999 |
| WO | WO 00/48510 | 8/2000 |
| WO | WO 00/51510 A1 | 9/2000 |
| WO | WO 00/62699 | 10/2000 |
| WO | WO 01/02042 A1 | 1/2001 |
| WO | WO 01/03642 | 1/2001 |
| WO | WO 01/10314 | 2/2001 |
| WO | WO 01/13839 | 3/2001 |
| WO | WO 01/13908 | 3/2001 |
| WO | WO 03/022221 | 3/2003 |

OTHER PUBLICATIONS

International search report and written opinion dated Aug. 17, 2007 for PCT/US2006/000221.

International search report and written opinion dated Feb. 7, 2012 for PCT/US2011/058157.

Becker et al., Lung Volumes Before and After Lung Volume Reduction Surgery, Am J Respir Crit Care Med, 1998; 157:1593-1599.

Burger et al., "Gas exchange in the parabronchial lung of birds: Experiments in unidirectionally ventilated ducks," Respiration Physiology 1979 Mar; 36(1):19-37.

Cotran et al., Chaper 15 in *Robbins Pathologic Basis of Disease*, 5th edition, eds., W.B. Saunders Company, Philadelphia, 1974, p. 683 - 694.

Criner et al., Effect of Lung vol. Reduction Surgery on Diaphragm Strength, Am J Respir Crit Care Med, 1998; 157:1578-1585.

Harada et al., Re-expansion of Refractory Atelectasis Using a Bronchofiberscope with a Balloon Cuff, Chest, 1983 Dec; 84:725-728.

Institute for Clinical Evaluative Sciences (ICES), "Endotracheal tube choice," 2001; retrieved from the Internet: <http://www.ices.on.ca/informed/periodical/subissue/133-ip7422.pdf>.

Kotloff et al., Comparison of Short-term Functional Outcomes Following Unilateral and Bilateral Lung vol. Reduction Surgery, Chest, 1998; 113:890-95.

Morrell et al., "Collateral ventilation and gas exchange during airway occlusion in the normal human lung," Am Rev Respir Dis. 1993 Mar;147(3):535-539.

Ojo et al., Lung vol. Reduction Surgery Alters Management of Pulmonary Nodules in Patients With Severe COPD, Chest, 1997; 112:1494-1500.

Raasch et al. Radiographic Anatomy of the Interlobar Fissure: A Study of r100 Specimens. AJR 1982; 138:1043-1049.

Sclafani, Clearing the Airways, AARC Times, Jan. 1999, pp. 69-72.

Woolcock et al., Mechanical Factors Influencing Collateral Ventilation in Human, Dog, And Pig Lungs, J Appl Physiol. 1971 Jan; 30(1):99-115.

* cited by examiner

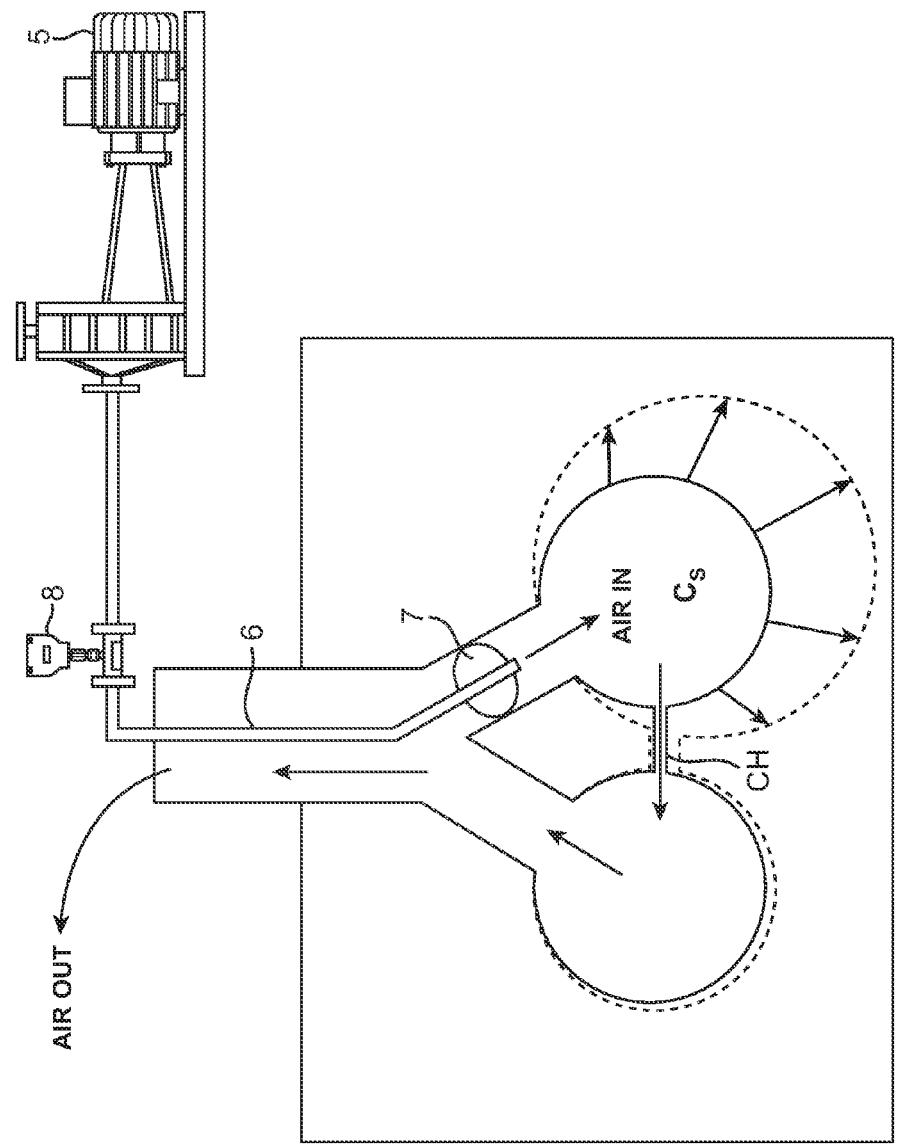
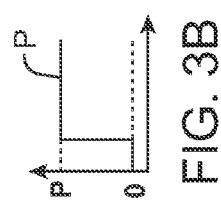
FIG. 3B
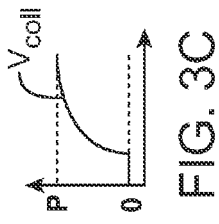
FIG. 3C
FIG. 3A
(PRIOR ART)

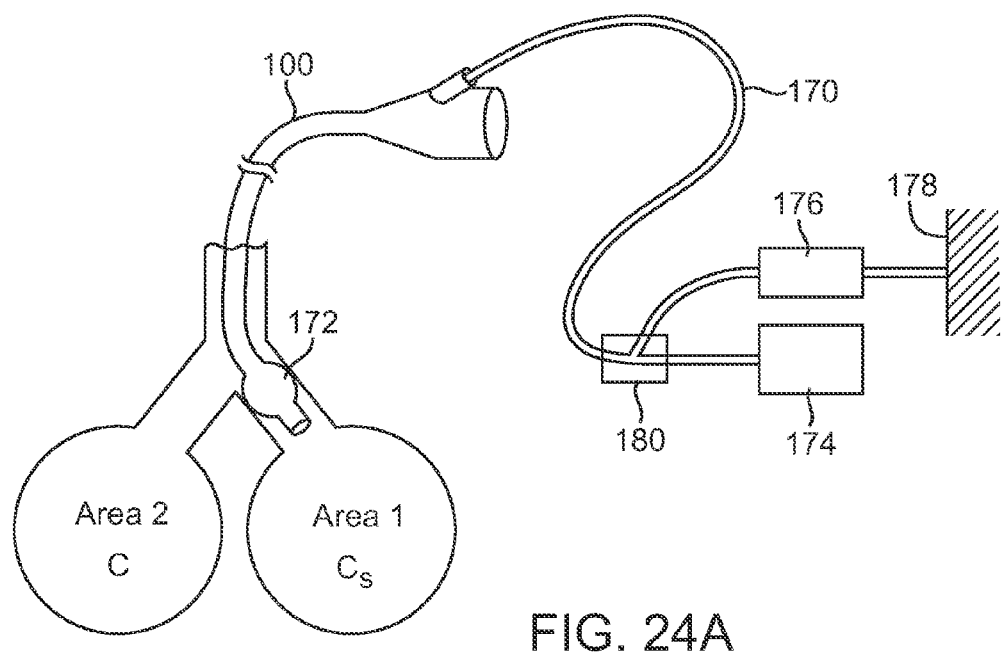
FIG. 24A
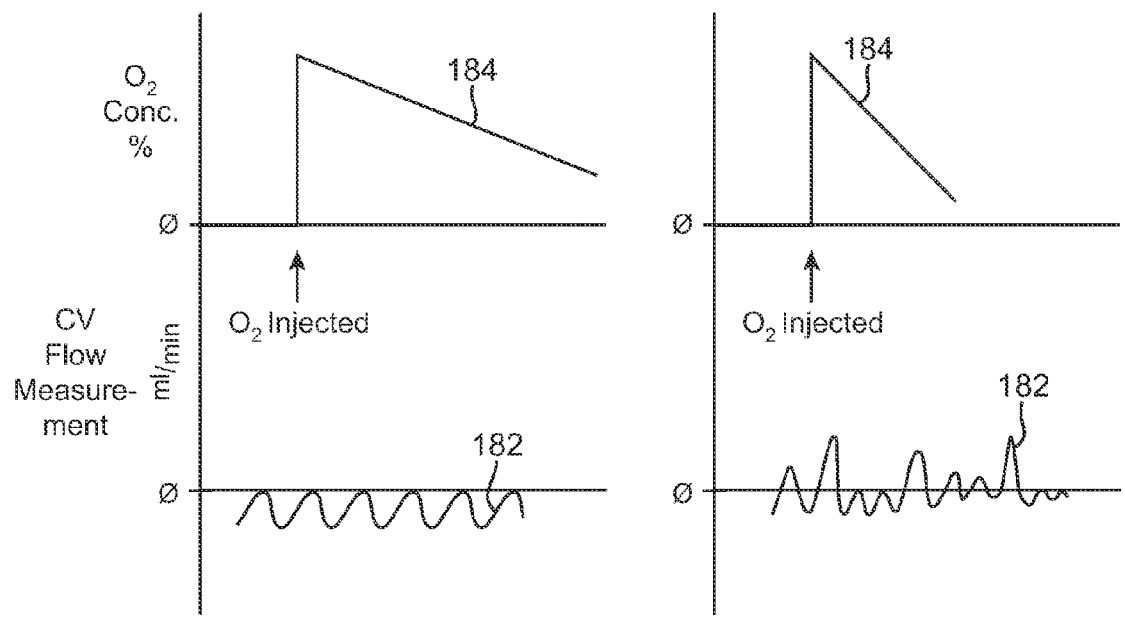
FIG. 24B
FIG. 24C

MINIMALLY INVASIVE DETERMINATION OF COLLATERAL VENTILATION IN LUNGS

CROSS-REFERENCES TO RELATED APPLICATIONS

This application is a divisional of U.S. patent application Ser. No. 11/296,951 filed Dec. 7, 2005, which is a continuation-in-part of U.S. patent application Ser. No. 10/241,733 filed Sep. 10, 2002, which claims priority to U.S. Provisional Patent Application No. 60/318,539 filed Sep. 10, 2001, and this application claims the benefit and priority of U.S. Provisional Patent Application No. 60/645,711, filed Jan. 20, 2005, U.S. Provisional Patent Application No. 60/696,940, filed Jul. 5, 2005, and U.S. Provisional Patent Application No. 60/699,289, filed Jul. 13, 2005, the full disclosures of all of which are hereby incorporated herein by reference.

BACKGROUND OF THE INVENTION

Field of the Invention

The present invention relates generally to respiratory medicine and more specifically to the field of assessing collateral ventilation pathways in the lung and quantitatively determining the resistance of these collateral ventilation pathways in the course of diagnosing and treating lung disease.

Because of recent advances in the treatment of chronic obstructive pulmonary disease (COPD) there has been a heightened interest in collateral ventilation. Various COPD treatments involve the removal of trapped air to reduce the debilitating hyperinflation caused by the disease and occlusion of the feeding bronchus to maintain the area at a reduced volume. The concept guiding these approaches is that aspiration and/or absorption atelectasis of emphysematous lung regions can reduce lung volume without the need to remove tissue. One such type of COPD treatment is Endobronchial Volume Reduction (EVR) uses a catheter-based system to reduce lung volume. With the aid of fiberoptic visualization and specialty catheters, a physician can selectively collapse a segment or segments of the diseased lung. An occlusal stent is then positioned within the lung segment to prevent the segment from reinflating.

FIGS. 1A-1C illustrate an example of such an EVR procedure targeting the right upper lobe RUL of the right lung RL of a patient. Here, the right upper lobe RUL is hyperinflated. A catheter 2 is advanced through the trachea T into the lung passageways feeding the right upper lobe RUL. The right upper lobe RUL is then reduced in volume, as illustrated in FIG. 1B, and a plug, valve or occlusal stent 4 is placed within the lung passageway reducing the volume of the right upper lobe RUL. However, as shown in FIG. 1C, collateral channels CH may be present connecting the right upper lobe RUL with the right middle lobe RML and/or the right lower lobe RLL. Consequently, the EVR may only be temporarily successful as the right upper lobe RUL re-expands or re-hyperinflates due to refill through the collateral channels CH over time. In some instances, effective EVR may not even be temporarily successful in that appropriate volume reduction may be impossible due to volume being drawn from neighboring lobes via the collateral channels CH.

FIGS. 2A-2B schematically illustrate example collateral channels CH in the right lung RL. FIG. 2A illustrates a variety of inter-lobar collateral channels CH between the right upper lobe RUL, right middle lobe RML and right lower lobe RLL. FIG. 2B illustrates intra-lobar or inter-segmental collateral channels CH which connect individual lung segments (e.g. $S$, $S_1$, $S_2$) within the lung lobes. These inter-segmental collateral channels allow the periphery of each of the lung compartments to communicate with one another and include well-known collateral pathways such as Martin's Channels, pores of Kohn and Lambert's canals. However, in healthy lungs, the main lobes (e.g RUL, RML, RLL) of the lung are typically separated from one another by impermeable fissures comprised of a double layer of infolded reflections of visceral pleura. Thus, in healthy lungs collateral channels CH between the lungs are considered not present or are minimal. Various anatomic studies have shown, however, that interlobar fissures frequently do not extend completely to the mediastinum or hilum and are, therefore, incomplete. In fact, various studies have described the major fissures to be incomplete in 18% to 73% of cases. As a result, there are varying degrees of fusion between lobes, and consequently, these areas of parenchymal fusion may provide a pathway for the spread of disease between lobes and a pathway for collateral air drift or inter-lobar collateral ventilation.

Further, a lesser known or rather overlooked fact is that, in the presence of COPD and emphysema, pathways also develop that traverse through the fissures thus interconnecting neighboring lung compartments. This has been demonstrated histologically by the use of tantalum gas. Tantalum dust has been shown to accumulate at gaps in the alveolar wall at the lobar junction and to pass through this area in isolated human lungs, some of which were from emphysema patients. Furthermore, there may be sufficient collateral air drift across incomplete major fissures in the dog to prevent atelectasis. Most importantly, the collateral airflow across incomplete major fissures has been measured in normal and emphysematous excised human lungs and it has been found that in emphysema it is markedly increased. The mechanism that allows for the creation of these inter-compartment collateral channels has not yet been documented in the scientific literature, however likely contributing factors are the elastin destruction that occurs in COPD and the tissue stretching that occurs with hyperinflation.

A method of measuring inter-compartment collateral ventilation has been to measure resistance to collateral ventilation ($R_{coll}$). Assessment of the relationship between steady-state flow through collateral channels ($Q_{coll}$) and the pressure drop across them is a direct way for measuring the resistance to collateral ventilation ($R_{coll}$). Many investigators have attempted to use this approach in the past but the most simple and versatile way to make this measurement was first described by Hilpert (Hilpert P. Kollaterale Ventilation Habilitationsschirift, aus der Medizinischen. Tubingen, West Germany: Tubingen Universitatsklinik, 1970. Thesis). This method is schematically illustrated in FIG. 3A-3C and includes supplying a constant positive pressure of air (P) to a target area or sealed target compartment $C_s$. The positive pressure of air is supplied by a positive pressure generator 5 through a double-lumen isolation catheter 6 having an isolation cuff 7 which is wedged into a peripheral airway and seals the compartment $C_s$. Therefore, any airflow out of the compartment $C_s$ is through collateral channels CH. FIG. 3B illustrates a state of steady pressure P. The method also includes determining the required airflow rate ($V_{coll}$) to maintain that pressure P. The airflow rate is measured by a flowmeter 8 disposed along the isolation catheter 6. The ratio of P over $V_{coll}$ provides a quantitative measure for the resistance to collateral ventilation. It may also be conceived that a constant airflow ($Q_{coll}$) may be injected through one lumen of the isolation catheter 6 while air pressure ($P_b$) at the site of bronchial obstruction is measured through the other lumen. Under steady-state conditions, the ratio between $P_b$ and $Q_{coll}$ equals the resistance through the collateral system, which includes the resistance in the collateral channels $R_{coll}$ and the resistance in the small airways $R_{saw}$ of the isolated compartment $C_s$ between the collateral channels CH and the distal end of the catheter 6. In either case, this technique can be somewhat useful as an experimental tool, however it has significant limitations experimentally and its clinical use poses an additional risk to the patient. Namely, applying positive pressure or constant air flow to a diseased area of the lung can be hazardous if not done correctly. For example in the presence of bullous emphysema, the pressure could enlarge the bullae or create new bulla, or could lead to increased hyperinflation or pneumothorax.

In another technique, the presence of inter-compartment collateral ventilation can be assessed by isolation of the target segment and subsequent introduction of the subject to breath normally with Heliox (21% $O_2$/79% He). Detection of tracer gas in the target segment indicates the presence of collateral channels communicating that area with the rest of the lung.

Experimental attempts to detect the presence of inter-compartmental collateral ventilation have also been described recently in excised deflated lungs wherein a lung area is cannulated, sealed and insufflated with air while separate neighboring lung areas are concurrently sealed, and observed to determine whether they inflate. Although this technique can prove very useful in the described experimental setting, its clinical practicality is undoubtedly severely limited for obvious reasons.

Another technique is described in US Patent Application US2003/0228344A1 in which a one-way valve is placed in the feeding bronchus of a area targeted for treatment such that air cannot pass in the inspiratory direction but can escape in the expiratory direction. The area is then observed radiographically to determine if absorption atelectasis eventually occurs; atelectasis would indicate the absence of collateral ventilation channels and the lack of atelectasis is alleged to be indicative of the presence of the collateral channels. Unfortunately this technique is difficult to practice because the one-way valve may not generate atelectasis for a variety of reasons such as mucus plugging of the valve, leakage, improper placement and the lack of a pressure gradient to force trapped air proximally across the valve.

Another method that imposes lesser risk to the patient, relatively to Hilpert's method, has been described by Woolcock and Macklem (Woolcock, A. J, and P. T. Macklem. Mechanical factors influencing collateral ventilation in human, dog, and pig lungs. J. Appl. Physiol. 30:99-115, 1971). This method involves the rapid injection of an air bolus beyond the wedged catheter into the target lung segment, and the rate at which pressure falls as the obstructed segment empties into the surrounding lung through collateral channels is governed by the time constant for collateral ventilation $\tau_{coll}$ (the time it takes for the pressure change produced by the air bolus injection to drop to about 37 percent of its initial value). Here $R_{coll}$ is indirectly measured as the ratio between $\tau_{coll}$ and the compliance of the target segment $C_s$. Calculations of $R_{coll}$ via this method, however, are highly dependent on several questionable assumptions, including homogeneity within the obstructed segment and in the surrounding lung. Values for $R_{coll}$ reported in the literature using either Hilpert's method or other methods range from approximately $10^{-1}$ to $10^{+2}$ $cmH_2O/(ml/s)$ for normal human lungs and from approximately $10^{-3}$ to $10^{-1}$ $cmH_2O/(ml/s)$ for emphysematous human lungs.

A direct, accurate, simple and minimally invasive method of assessing collateral flow in lungs is desired, which also poses minimal risk to the patient. In addition, methods and devices for quantitatively determining the resistance of these collateral ventilation pathways in the course of diagnosing and treating lung disease is also desired. At least some of these objectives will be met by the present invention.

BRIEF SUMMARY OF THE INVENTION

Minimally invasive methods, systems and devices are provided for qualitatively and quantitatively assessing collateral ventilation in the lungs. In particular, collateral ventilation of a target compartment within a lung of a patient is assessed by advancement of a catheter through the tracheobronchial tree to a feeding bronchus of the target compartment. The feeding bronchus is occluded by the catheter and a variety of measurements are taken with the use of the catheter in a manner which is of low risk to the patient. Examples of such measurements include but are not limited to flow rate and pressure. These measurements are used to determine the presence of collateral ventilation and to quantify such collateral ventilation. Collateral ventilation refers to flow or passage of air from the target lung compartment into one or more adjacent components through passage(s) in or through the natural barriers which form the components.

Consequently, the lungs of a patient may be analyzed for appropriateness of various treatment options prior to treatment. For example, levels of collateral ventilation may be mapped to various target compartments so that the practitioner may determine the overall condition of the patient and the most desired course of treatment. If it is desired to perform Endobronchial Volume Reduction (EVR) on a lung compartment, the lung compartment may be analyzed for collateral ventilation prior to treatment to determine the likelihood of success of such treatment. Further, if undesired levels of collateral ventilation are measured, the collateral ventilation may be reduced to a desired level prior to treatment to ensure success of such treatment. Thus, methods, systems and devices of the present invention provide advantages over conventional trial-and-error methodologies in which treatment plans are determined blindly, without such diagnostic information. This increases the likelihood of successful treatment and reduces time, cost and complications for the patient.

In a first aspect of the present invention, methods are provided for diagnosing collateral ventilation between a target lung compartment and adjacent lung compartment(s) in a patient. In some embodiments, the method comprises isolating a target lung compartment from at least one adjacent lung compartment(s) usually all adjacent compartments, and allowing the patient to breathe air free from the introduced markers and detecting air flow or accumulation from the isolated lung compartment over time. Typically, isolating comprises introducing a catheter transtracheally to a main bronchus feeding into the target lung compartment and deploying an occlusion member on the catheter to isolate the target lung compartment in the main passageway leading into that compartment. In some instances, detecting may comprise measuring air flow through a lumen in the catheter while the patient exhales, wherein said air entered the isolated compartment via collateral passages while the patient inhaled. In other instances, detecting comprises accumulating air from the isolated compartment air from the isolated compartment through the catheter over a number of successive breathing cycles, wherein a continuous increase in accumulated air volume indicates collateral flow into the isolated compartment.

In another aspect of the present invention, methods are provided for determining the function or malfunction of an endobronchial prosthesis positioned within a lung passageway of a patient. In some embodiments, the method comprises occluding the lung passageway proximally of the endobronchial prosthesis, allowing the patient to breathe air without any markers, and measuring air flow or accumulation from the lung passageway over time wherein said measurement is correlative to the function or malfunction of the endobronchial prosthesis.

In a further aspect of the present invention, systems are provided for detecting collateral ventilation into a lung compartment in a patient. In some embodiments, the system comprises a catheter adapted to be introduced transtracheally to a bronchus leading to a target lung compartment, an occlusion member on a distal region of the catheter, said occlusion member being adapted to selectively occlude the bronchus, and a flow measurement sensor on the catheter to detect flow of air from the isolated compartment as the patient exhales.

In yet another aspect of the present invention, systems are provided for detecting collateral ventilation into a lung compartment in a patient. In some embodiments, the system comprises a catheter adapted to be introduced transtracheally to a bronchus leading to a target lung compartment, an occlusion member or a distal region of the catheter, said occlusion member being adapted to selectively occlude the bronchus and an accumulator connectable to the catheter to accumulate air exhaled from the catheter over time. Examples of accumulators include a slack collection bag which has substantially no resistance to filling with air.

In another aspect of the present invention, methods are provided for evaluating a target lung compartment of a patient. In some embodiments, the method comprises positioning an instrument within a lung passageway leading to the target lung compartment so that the target lung compartment is isolated, injecting an inert gas into the isolated target lung compartment, generating at least one measurement of pressure within the target lung segment, generating at least one measurement of concentration of inert gas within the target lung segment, and analyzing the at least one target lung compartment with the use of the at least one measurement of pressure and the at least one measurement of concentration of inert gas. Analyzing may comprise determining a degree of hyperinflation. In such instances, the method may further comprise determining a treatment plan at least partially based on the determined degree of hyperinflation. Alternatively or in addition, analyzing may comprise determining a state of compliance. In such instances, the method may further comprise determining a treatment plan at least partially based on the determined state of compliance. Likewise, analyzing may comprise determining a collateral resistance. In such instances, the method may further comprise determining a treatment plan based on the determined collateral resistance.

In some embodiments, generating the at least one measurement of pressure comprises generating a plurality of measurements of pressure over a predetermined time period. The predetermined time period may comprise, for example, approximately one minute. In some embodiments, generating the at least one measurement of concentration of inert gas comprises generating a plurality of measurements of concentration of inert gas over a predetermined time period. The predetermined time period may comprise, for example, approximately one minute. Further, the inert gas may comprise helium.

In another aspect of the present invention, systems are provided for evaluating a target lung compartment comprising an instrument positionable within a lung passageway leading to the target lung compartment so that the target lung compartment is isolated, wherein the instrument includes a mechanism for injecting an inert gas to the target lung segment, at least one sensor which generates measurement data reflecting pressure within the target lung segment, and at least one sensor which generates measurement data reflecting concentration of an inert gas within the target lung segment. In some embodiments, the system further comprises a processor which performs computations with the use of the measurement data reflecting pressure and the measurement data reflecting concentration of inert gas. In these embodiments, the computations may include calculating a degree of hyperinflation of the target lung compartment, calculating a state of compliance of the target lung compartment, and/or calculating collateral resistance of the target lung compartment. The measurement data reflecting pressure may comprise generating a plurality of measurements of pressure over a predetermined time period. In some instances, the predetermined time period comprises approximately one minute. The measurement data reflecting concentration of inert gas may comprise generating a plurality of measurements of concentration of inert gas over a predetermined time period. In some instances, the predetermined time period comprises approximately one minute. In addition, the inert gas may comprise helium.

In another aspect of the present invention, treatment guides are provided to determine a course of treatment for a lung compartment of a patient. In some embodiments, the guide comprises a plurality of hyperinflation values, each hyperinflation value representing a degree of hyperinflation of the lung compartment, and/or a plurality of compliance values, each compliance value representing a degree of compliance of the lung compartment, and a plurality of treatment options, wherein each treatment option is correlated to a hyperinflation value and/or a compliance value. Typically, the guide comprises a computer program. In such instances, the computer program includes at least one mathematical computation to generate the plurality of hyperinflation values and/or the plurality of compliance values. The mathematical computation may utilize, for example, pressure and concentration of inert gas values.

In still another aspect of the present invention, methods of evaluating collateral ventilation of a target lung compartment of a patient are provided. In some embodiments, the method includes positioning an instrument within a lung passageway leading to the target lung compartment so that the target lung compartment is isolated, allowing the patient to inhale air, generating at least one measurement of at least one characteristic of the inhaled air within or exiting the target lung compartment with the use of the instrument, and determining a level of collateral ventilation into the target lung compartment based on the at least one measurement. Typically, the at least one characteristic includes volumetric flow rate and pressure. Determining a level of collateral ventilation may include calculating a value of collateral resistance. The method may further comprise determining a treatment plan based on the level of collateral ventilation.

In yet another aspect of the present invention, methods are provided for evaluating a patient for treatment of a target lung compartment, the method comprising generating at least one measurement associated with the target lung compartment while the patient is breathing air, calculating a level of collateral ventilation into the target lung compartment based on the at least one measurement, and treating the patient based on the calculated level of collateral ventilation. Treating the patient may comprise aspirating the target lung compartment. Alternatively or in addition, treating the patient may comprise occluding a lung passageway feeding the target lung compartment. Typically, occluding comprises positioning an occlusal stent within the lung passageway. Calculating may comprise calculating a value of collateral resistance based on the at least one measurement.

In a further aspect of the present invention, additional treatment guides are provided to determine a course of treatment for a lung compartment of a patient. In some embodiments, the guide comprises a plurality of collateral resistance values, each value representing degree of collateral ventilation of the lung compartment, and a plurality of treatment options, wherein each treatment option is correlated to a collateral resistance value. Typically, the guide comprises a computer program. In such instances, the computer program may include at least one mathematical computation to generate the plurality of collateral resistance values. The mathematical computation may utilize pressure and volumetric flow rate values. In some embodiments, the guide also includes a visual display showing a curve representing a relationship between the collateral resistance values and a combination of the pressure and volumetric flow rates.

Other objects and advantages of the present invention will become apparent from the detailed description to follow, together with the accompanying drawings.

BRIEF DESCRIPTION OF THE DRAWINGS

FIGS. 3A-3C schematically illustrates a method of supplying constant positive pressure of air to a target compartment.

FIGS. 24A-24C illustrate the use of oxygen to indicate collateral flow.

DETAILED DESCRIPTION OF THE INVENTION

Minimally invasive methods, systems and devices are provided for qualitatively and quantitatively assessing collateral ventilation in the lungs. FIGS. 4A-4D illustrate an embodiment of a minimally invasive method in which a catheter 10 is advanced through a tracheobronchial tree to the feeding bronchus B of the target area $C_s$, the compartment targeted for treatment or isolation. The catheter 10 comprises a shaft 12 having at least one lumen therethrough and an occlusion member 14 mounted near its distal end. The catheter 10 is equipped to seal the area between the catheter shaft 12 and the bronchial wall such that only a lumen inside the catheter which extends the entire length of the catheter is communicating with the airways distal to the seal. The seal, or isolation, is accomplished by the use of the occlusion member 14, such as an inflatable member, attached to the distal tip of the catheter 10.

Figure 1A:
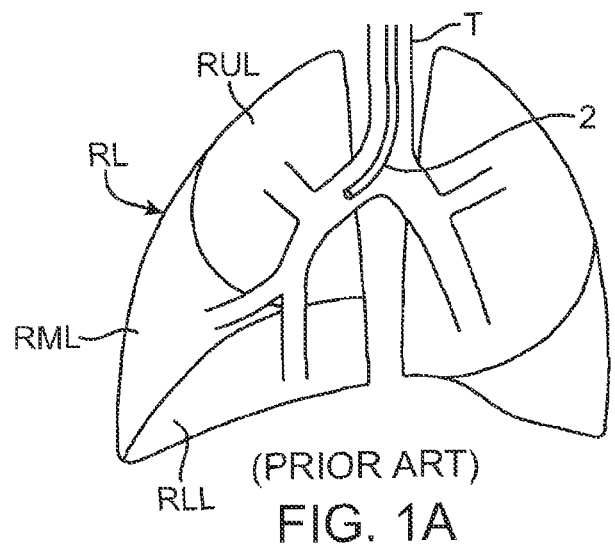
FIGS. 1A-1C illustrate an example of an EVR procedure targeting the right upper lobe of the right lung of a patient.
Figure 1B:
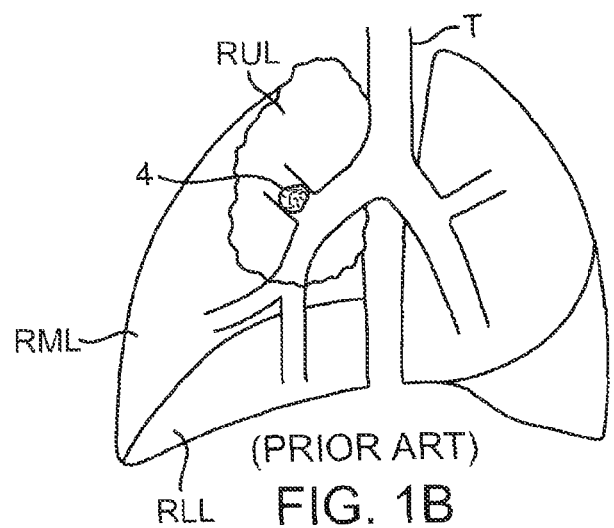
Figure 1C:
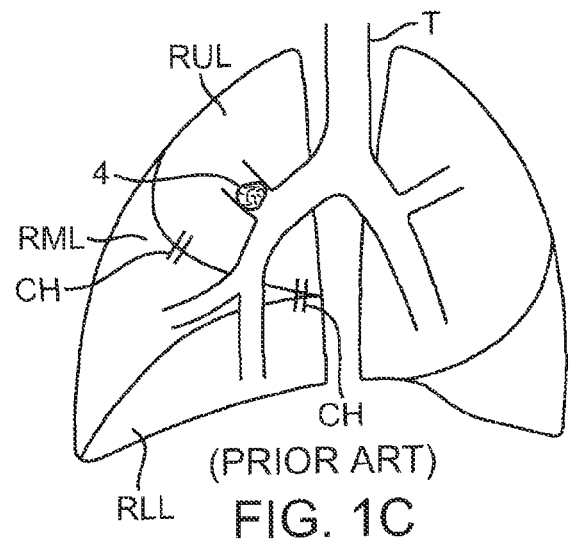
Figure 2A:
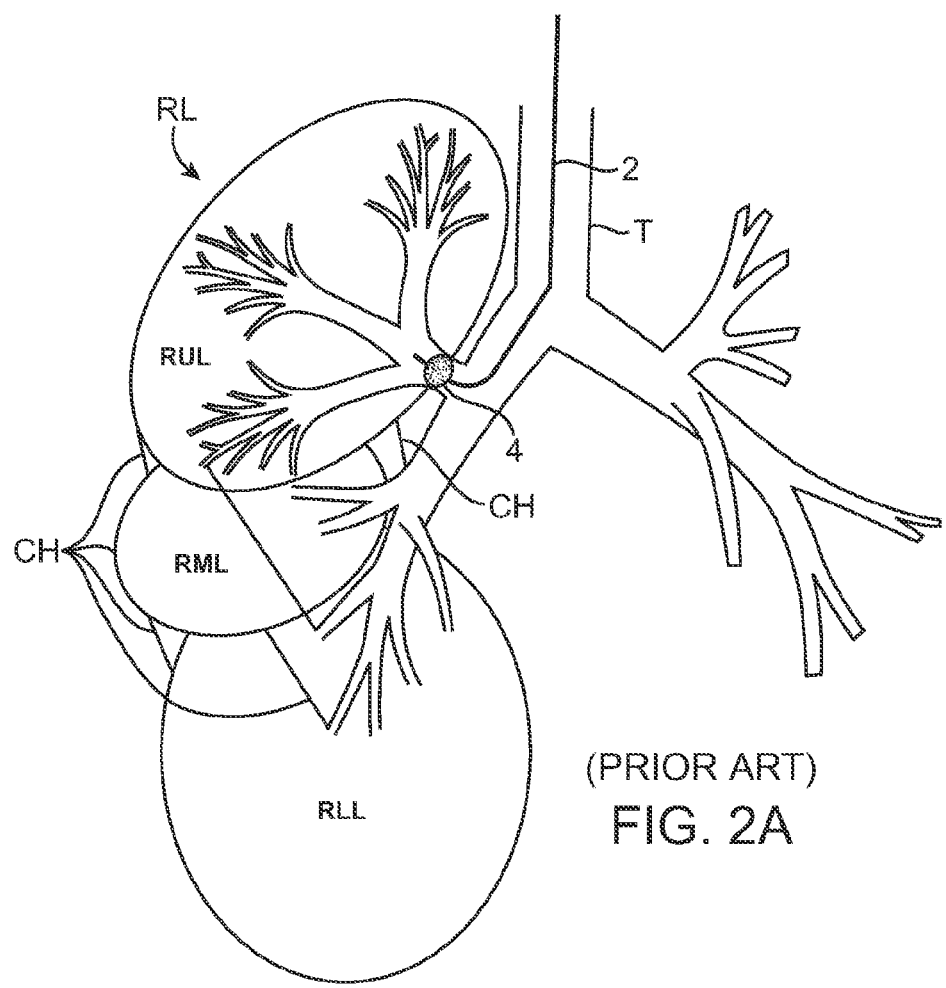
FIGS. 2A-2B schematically illustrate example collateral channels in the right lung.
Figure 2B:
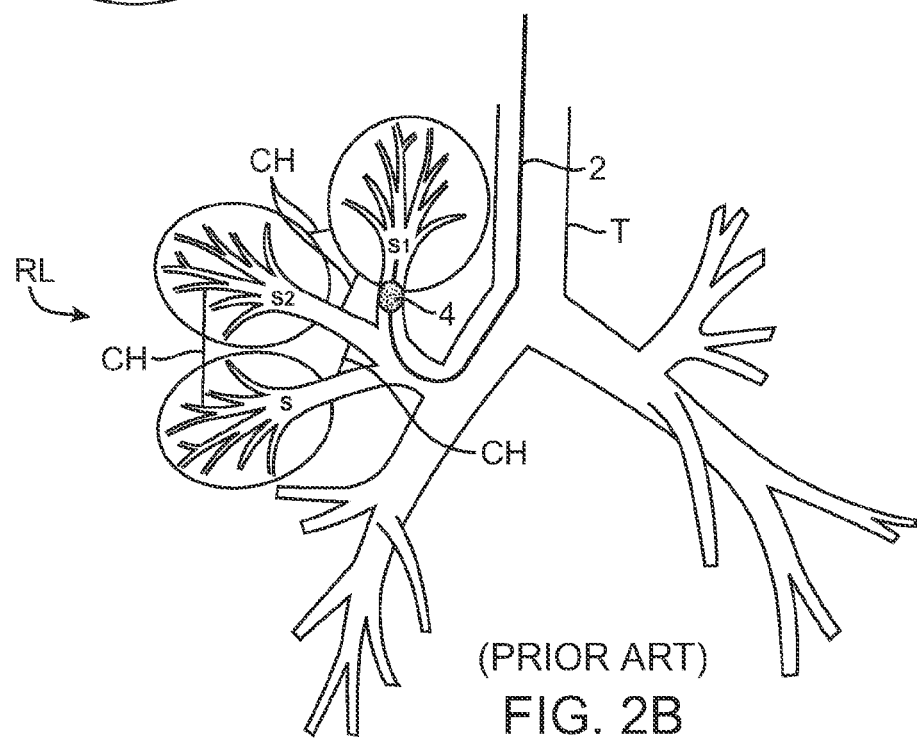
Figure 4A:
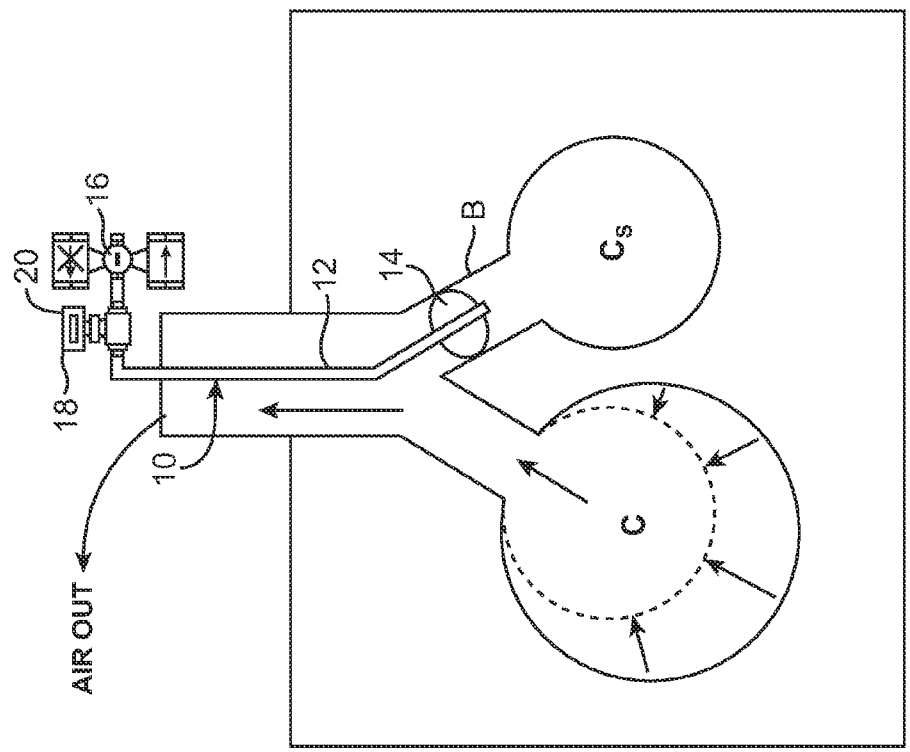
FIGS. 4A-4D illustrate an embodiment of a minimally invasive method in which a catheter is advanced to the feeding bronchus of a target compartment.
Figure 4B:
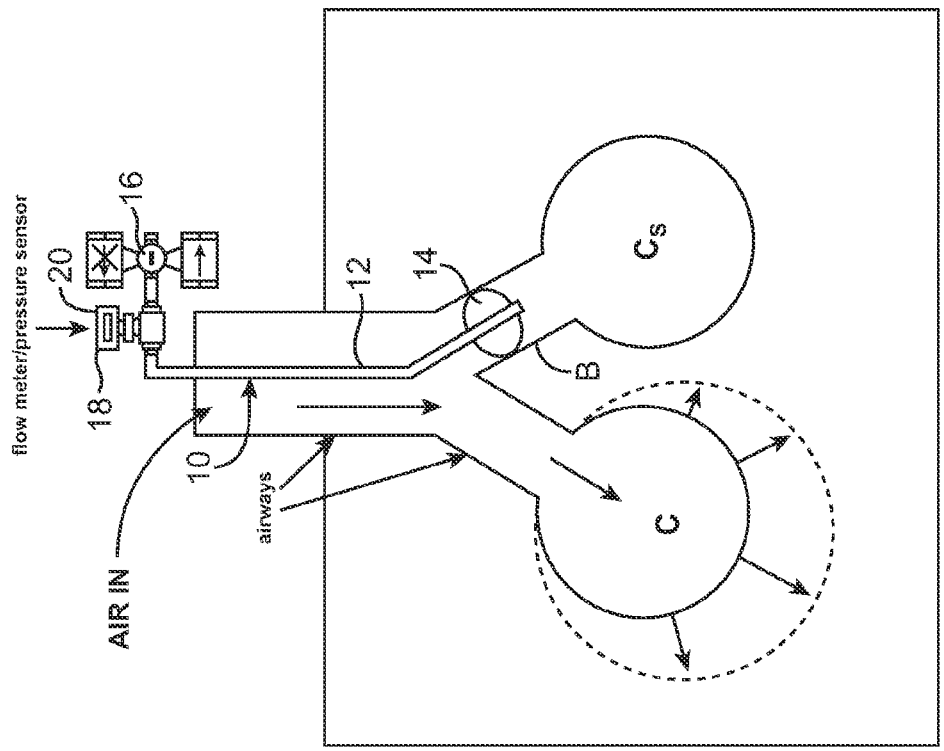
Figure 4D:
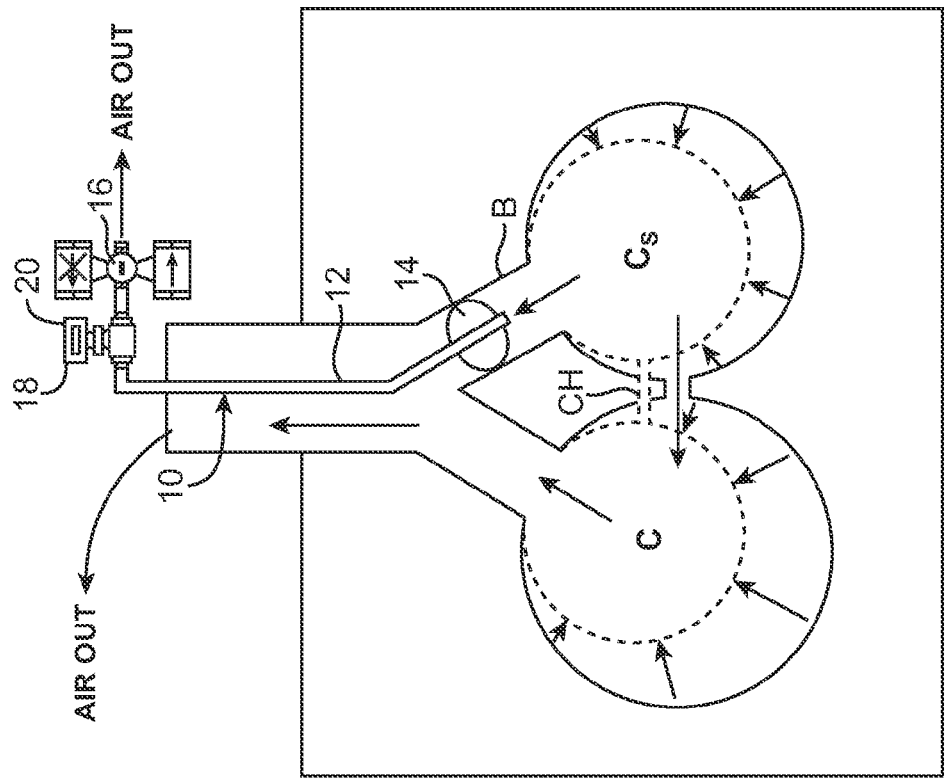
Figure 4C:
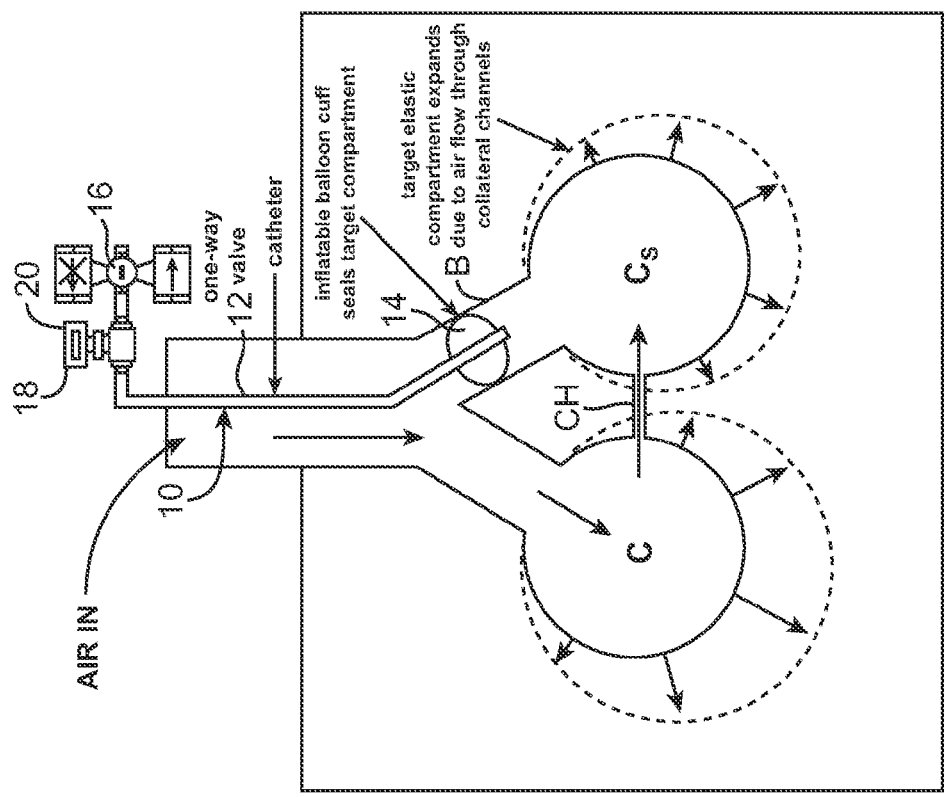

On the opposite end of the catheter 10, external to the body of the patient, a one-way valve 16, a flow-measuring device 18 or/and a pressure sensor 20 are placed in series so as to communicate with the catheter's inside lumen. The one-way valve 16 prevents air from entering the target compartment $C_s$ from atmosphere but allows free air movement from the target compartment $C_s$ to atmosphere. When there is an absence of collateral channels connecting the targeted isolated compartment $C_s$ to the rest of the lung, as illustrated in FIGS. 4A-4B, the isolated compartment $C_s$ will unsuccessfully attempt to draw air from the catheter lumen during inspiration of normal respiration of the patient. Hence, during exhalation no air is returned to the catheter lumen. In the presence of collateral channels, as illustrated in FIGS. 4C-4D, an additional amount of air is available to the isolated compartment $C_s$ during the inspiratory phase of each breath, namely the air traveling from the neighboring compartment(s) C through the collateral channels CH, which enables volumetric expansion of the isolated compartment $C_s$ during inspiration, resulting during expiration in air movement away from the isolated compartment $C_s$ to atmosphere through the catheter lumen and the collateral channels CH. Thus, air is expelled through the catheter lumen during each exhalation and will register as positive airflow on the flow-measuring device 18. This positive airflow through the catheter lumen provides an indication of whether or not there is collateral ventilation occurring in the targeted compartment $C_s$.

This technique of measuring collateral flow in a lung compartment is analogous to adding another lung compartment, or lobe with infinitely large compliance, to the person's lungs, the added compartment being added externally. Depending on the system dynamics, some air may be expelled through the catheter lumen during exhalation in the absence of collateral channels, however at a different rate, volume and trend than that in the presence of collateral channels.

Figure 5B:
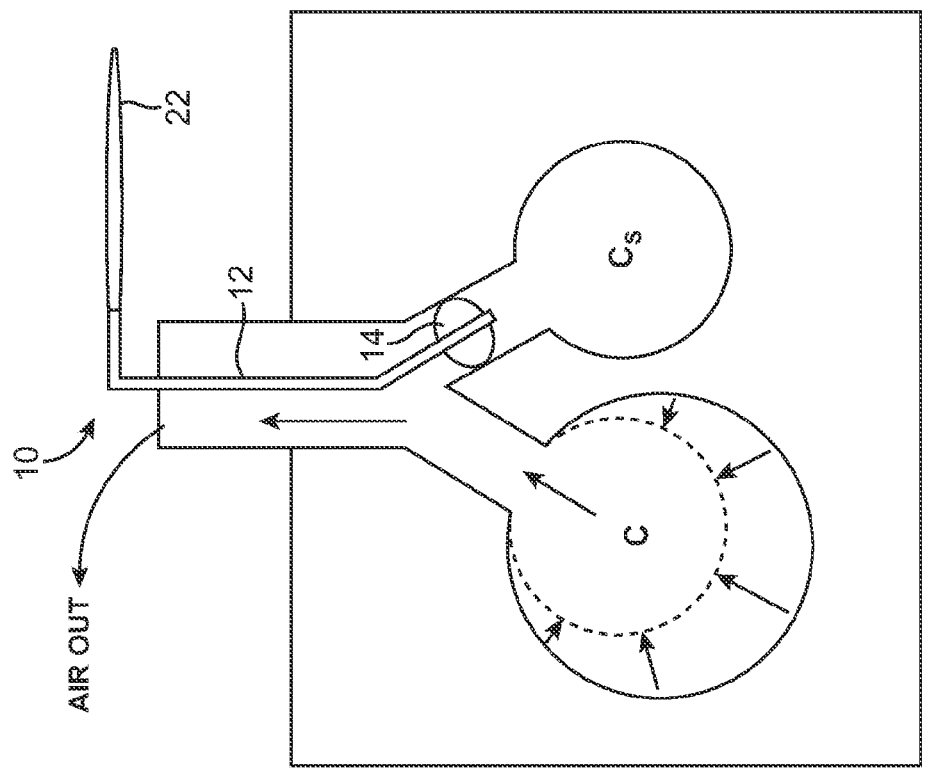
FIGS. 5A-5D, 6 illustrate embodiments of a catheter connected with an accumulator.
Figure 5A:
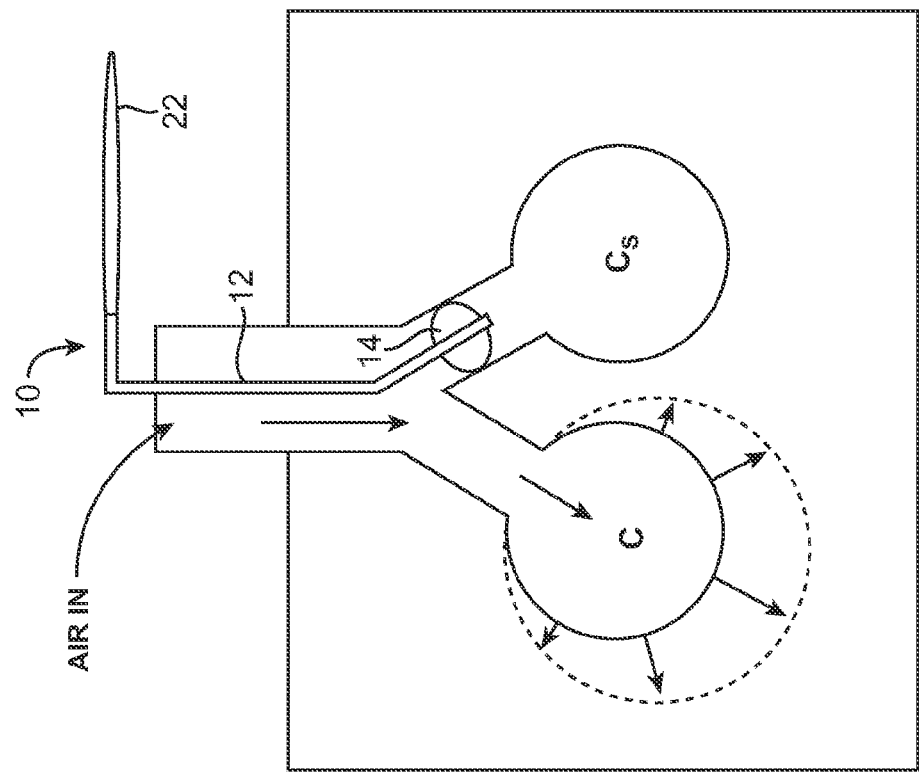
Figure 5C:
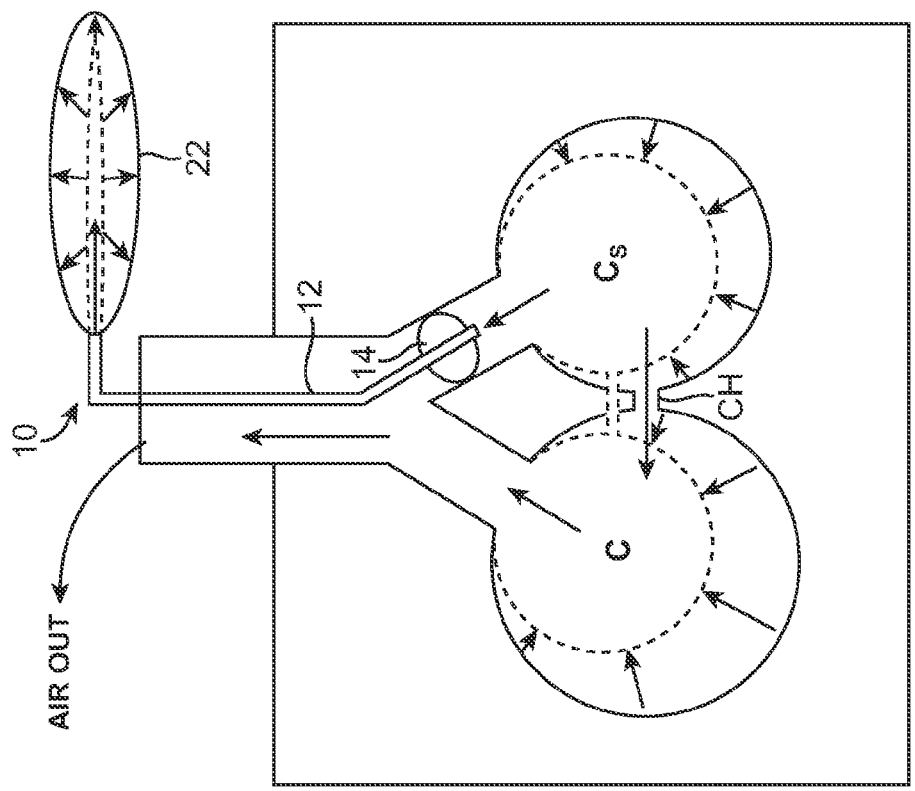
Figure 5D:
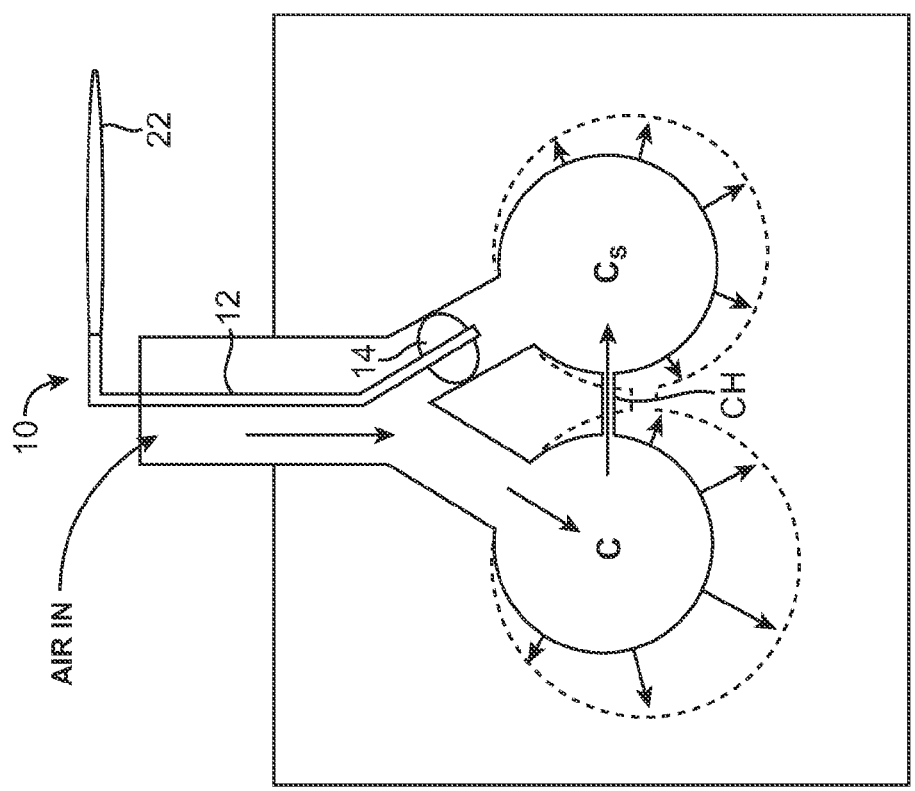

In other embodiments, the catheter 10 is connected with an accumulator or special container 22 as illustrated in FIGS. 5A-5D, 6. The container 22 has a very low resistance to airflow, such as but not limited to e.g. a very compliant bag or slack collection bag. The container 22 is connected to the external end or distal end 24 of the catheter 10 and its internal lumen extending therethrough in a manner in which the inside of the special container 22 is communicating only with the internal lumen. During respiration, when collateral channels are not present as illustrated in FIGS. 5A-5B, the special container 22 does not expand. The target compartment Cs is sealed by the isolation balloon 14 so that air enters and exits the non-target compartment C. During respiration, in the presence of collateral channels as illustrated in FIGS. 5C-5D, the special container 22 will initially increase in volume because during the first exhalation some portion of the airflow received by the sealed compartment $C_s$ via the collateral channels CH will be exhaled through the catheter lumen into the external special container 22. The properties of the special container 22 are selected in order for the special container 22 to minimally influence the dynamics of the collateral channels CH, in particular a highly inelastic special container 22 so that it does not resist inflation. Under the assumption that the resistance to collateral ventilation is smaller during inspiration than during expiration, the volume in the special container 22 will continue to increase during each subsequent respiratory cycle because the volume of air traveling via collateral channels CH to the sealed compartment $C_s$ will be greater during inspiration than during expiration, resulting in an additional volume of air being forced through the catheter lumen into the special container 22 during exhalation.

Figure 6:
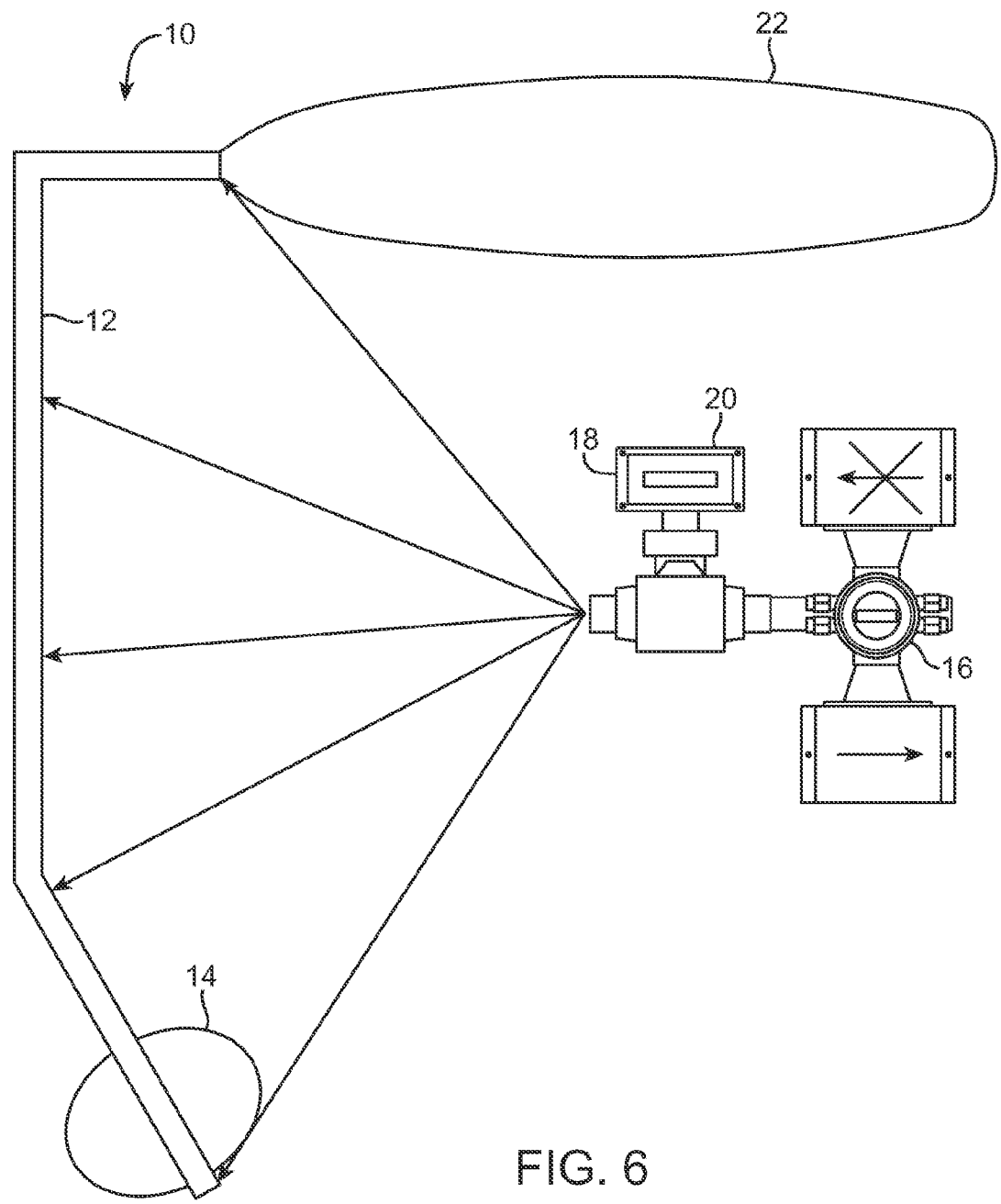

Optionally, a flow-measuring device 18 or/and a pressure sensor 20 may be included, as illustrated in FIG. 6. The flow-measuring device 18 and/or the pressure sensor 20 may be disposed at any location along the catheter shaft 12 (as indicated by arrows) so as to communicate with the catheter's internal lumen. When used together, the flow-measuring device 18 and the pressure sensor 20 may be placed in series. A one-way valve 16 may also be placed in series with the flow-measuring device 18 or/and pressure sensor 20. It may be appreciated that the flow-measuring device 18 can be placed instead of the special container 22 or between the special container 22 and the isolated lung compartment, typically at but not limited to the catheter-special container junction, to measure the air flow rate in and out of the special container and hence by integration of the flow rate provide a measure of the volume of air flowing through the catheter lumen from/to the sealed compartment $C_s$.

It can be appreciated that measuring flow can take a variety of forms, such as but not limited to measuring flow directly with the flow-measuring device 18, and/or indirectly by measuring pressure with the pressure sensor 20, and can be measured anywhere along the catheter shaft 12 with or without a one-way valve 16 in conjunction with the flow sensor 18 and with or without an external special container 22.

Furthermore, a constant bias flow rate can be introduced into the sealed compartment $C_s$ with amplitude significantly lower than the flow rate expected to be measured due to collateral flow via the separate lumen in the catheter 10. For example, if collateral flow measured at the flow meter 18 is expected to be in the range of 1 ml/min, the bias flow rate can be, but not limited to one tenth (0.1) or one one-hundredth (0.01) of that amount of equal or opposite amplitude. The purpose of the bias flow is to continuously detect for interruptions in the detection circuit (i.e., the working channel of the bronchoscope and any other tubing between the flow meter and catheter) such as kinks or clogs, and also to increase response time in the circuit (due to e.g. inertia). Still, a quick flush of gas at a high flow rate (which is distinguished from the collateral ventilation measurement flow rate) can periodically be introduced to assure an unclogged line.

In addition to determining the presence of collateral ventilation of a target lung compartment, the degree of collateral ventilation may be quantified by methods of the present invention. In one embodiment, the degree of collateral ventilation is quantified based on the resistance through the collateral system $R_{coll}$. $R_{coll}$ can be determined based on the following equation:

$$\left|\frac{\overline{P_b}}{\overline{Q_{fm}}}\right| = R_{coll} + R_{saw} \quad (1)$$

where $R_{coll}$ constitutes the resistance of the collateral channels, $R_{saw}$ characterizes the resistance of the small airways, and $\overline{P_b}$ and $\overline{Q_{fm}}$ represent the mean pressure and the mean flow measured by a catheter isolating a target lung compartment in a manner similar to the depictions of FIGS. 4A-4D.

Figure 7A:
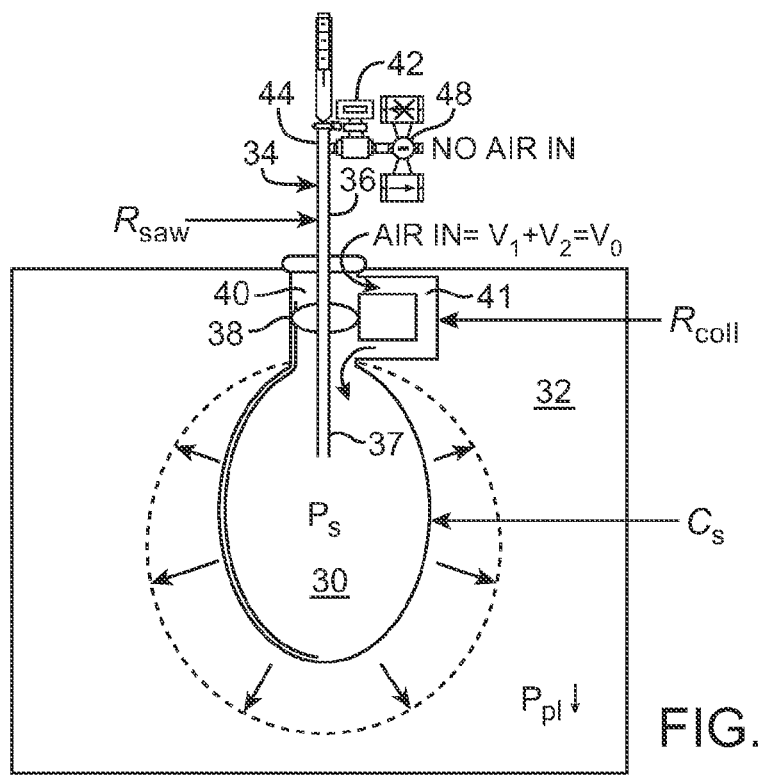
FIGS. 7A-7B depict a graphical representation of a simplified collateral system of a target lung compartment.
Figure 7B:
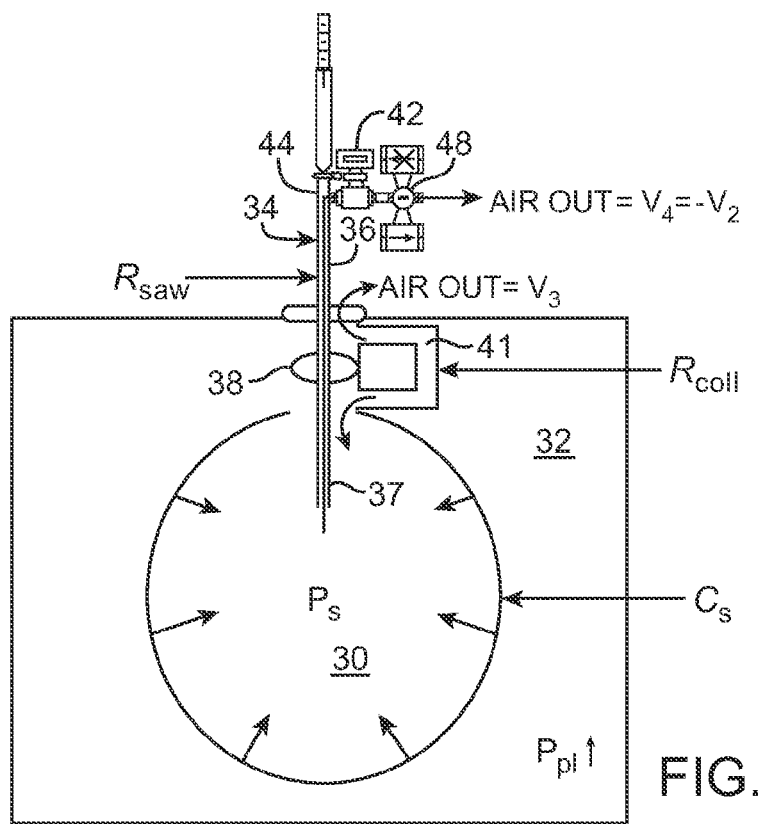

For the sake of simplicity, and as a means to carry out a proof of principle, FIGS. 7A-7B depict a graphical representation of a simplified collateral system of a target lung compartment $C_s$. A single elastic compartment 30 represents the target lung compartment $C_s$ and is securely positioned inside a chamber 32 to prevent any passage of air between the compartment 30 and the chamber 32. The chamber 32 can be pressurized to a varying negative pressure relative to atmosphere, representing the intrathoracic pressure $P_{pl}$. The elastic compartment 30, which represents the target compartment in the lung $C_s$, communicates with the atmospheric environment through passageway 40. In addition, the elastic compartment 30 also communicates with the atmospheric environment through collateral pathway 41, representing collateral channels CH of the target compartment of the lung $C_s$.

A catheter 34 is advanceable through the passageway 40, as illustrated in FIGS. 7A-7B. The catheter 34 comprises a shaft 36, an inner lumen 37 therethrough and an occlusion member 38 mounted near it's distal end. The catheter 34 is specially equipped to seal the area between the catheter shaft 36 and the passageway 40 such that only the lumen 37 inside the catheter 34, which extends the length of the catheter 34, allows for direct communication between the compartment 30 and atmosphere. On the opposite end of the catheter 34, a flow-measuring device 42 and a pressure sensor 44 are placed in series to detect pressure and flow in the catheter's inside lumen 37. A one-way valve 48 positioned next to the flow measuring device 42 allows for the passage of air in only one direction, namely from the compartment 30 to atmosphere. The flow measuring device 42, the pressure sensor device 44 and the one-way valve 48 can be placed anywhere along the length of the catheter lumen, typically at but not limited to the proximal end of the catheter shaft 36. It should be appreciated that measuring pressure inside the compartment 30 can be accomplished in a variety of forms, such as but not limited to connecting the pressure sensor 44 to the catheter's inside lumen 37. For instance, it can also be accomplished by connecting the pressure sensor 44 to a separate lumen inside the catheter 34, which extends the entire length of the catheter 34 communication with the airways distal to the seal.

At any given time, the compartment 30 may only communicate to atmosphere either via the catheter's inside lumen 37 representing $R_{saw}$ and/or the collateral pathway 41 representing $R_{coll}$. Accordingly, during inspiration, as illustrated in FIG. 7A, $P_{pl}$ becomes increasingly negative and air must enter the compartment 30 solely via collateral channels 41. Whereas during expiration, illustrated in FIG. 7B, air may leave via collateral channels 41 and via the catheter's inside lumen 37.

Figure 8A:
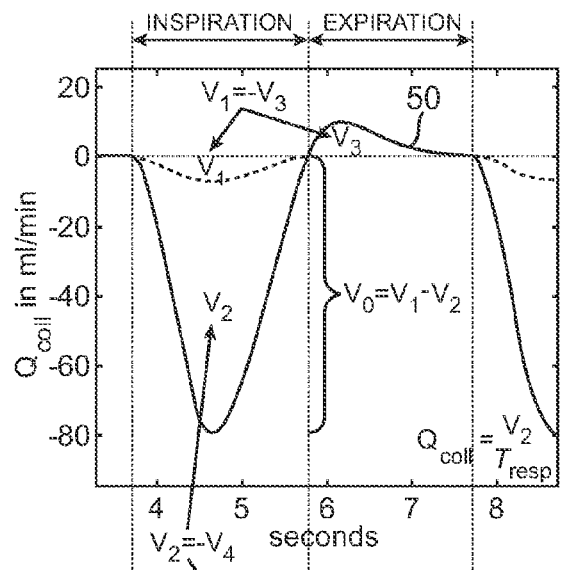
FIGS. 8A-8C illustrate measurements taken from the system of FIGS. 7A-7B.
Figure 8B:
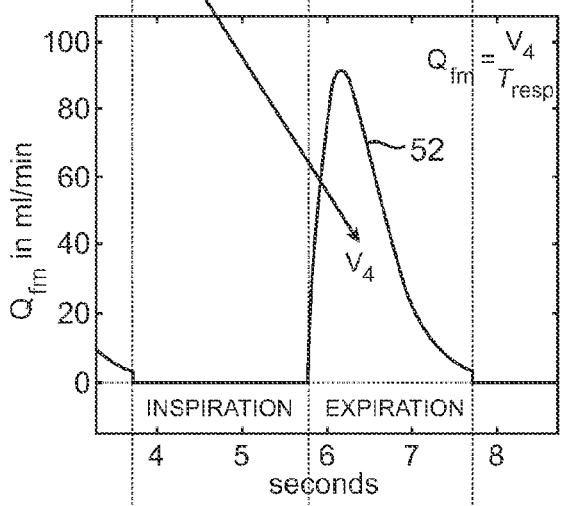
Figure 8C:
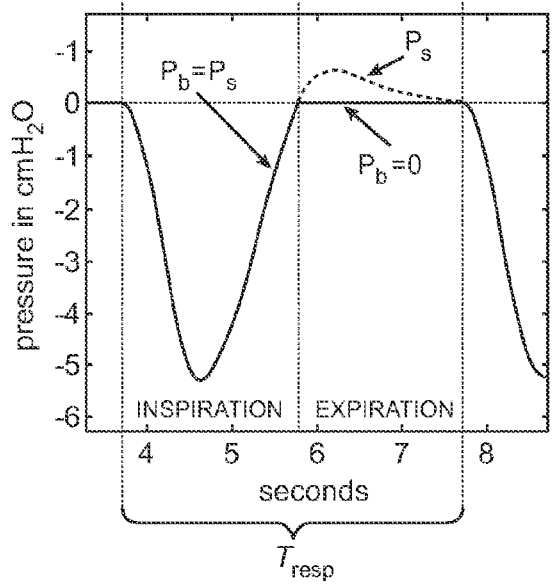

FIGS. 8A-8C illustrate measurements taken from the system of FIGS. 7A-7B during inspiration and expiration phases. FIG. 8A illustrates a collateral flow curve 50 reflecting the flow $Q_{coll}$ through the collateral pathway 41. FIG. 8B illustrates a catheter flow curve 52 reflecting the flow $Q_{fm}$ through the flow-measuring device 42. During inspiration, air flows through the collateral pathway 41 only; no air flows through the flow-measuring device 42 since the one-way valve 48 prevents such flow. Thus, FIG. 8A illustrates a negative collateral flow curve 50 and FIG. 8B illustrates a flat, zero-valued catheter flow curve 52. During expiration, a smaller amount of air, as compared to the amount of air entering the target compartment Cs during inspiration, flows back to atmosphere through the collateral pathway 41, as illustrated by the positive collateral flow curve 50 of FIG. 8A, while the remaining amount of air flows through the catheter lumen 37 back to atmosphere, as illustrated by the positive catheter flow curve 52 of FIG. 8B.

The volume of air flowing during inspiration and expiration can be quantified by the areas under the flow curves 50, 52. The total volume of air $V_0$ entering the target compartment 30 via collateral channels 41 during inspiration can be represented by the colored area under the collateral flow curve 50 of FIG. 8A. The total volume of air $V_0$ may be denoted as $V_0 = V_1 + V_2$, whereby $V_1$ is equal to the volume of air expelled via the collateral channels 41 during expiration (indicated by the grey-colored area under the collateral flow curve 50 labeled $V_3$), and $V_2$ is equal to the volume of air expelled via the catheter's inside lumen 37 during expiration (indicated by the colored area under the catheter flow curve 52 of FIG. 8B labeled $V_4$).

The following rigorous mathematical derivation demonstrates the validity of theses statements and the relation stated in Eq. 1:

Conservation of mass states that in the short-term steady state, the volume of air entering the target compartment 30 during inspiration must equal the volume of air leaving the same target compartment 30 during expiration, hence $$V_0 = -(V_3 + V_4) \qquad (2)$$

Furthermore, the mean rate of air entering and leaving the target compartment solely via collateral channels during a complete respiratory cycle ($T_{resp}$) can be determined as $$\overline{Q_{coll}} = \frac{V_0 + V_3}{T_{resp}} = \frac{V_2}{T_{resp}} \qquad (3)$$

where $V_2$ over $T_{resp}$ represents the net flow rate of air entering the target compartment 30 via the collateral channels 41 and returning to atmosphere through a different pathway during $T_{resp}$. Accordingly, $V_2$ accounts for a fraction of $V_0$, the total volume of air entering the target compartment 30 via collateral channels 41 during $T_{resp}$, hence $V_0$ can be equally defined in terms of $V_1$ and $V_2$ as $$V_0 = V_1 + V_2 \qquad (4)$$

where $V_1$ represents the amount of air entering the target compartment 30 via the collateral channels 41 and returning to atmosphere through the same pathway. Consequently, substitution of $V_0$ from Eq. 4 into Eq. 3 yields $$V_1 = -V_3 \qquad (5)$$

and substitution of $V_0$ from Eq. 2 into the left side of Eq. 4 following substitution of $V_1$ from Eq. 5 into the right side of Eq. 4 results in $$-V_4 = V_2 \qquad (6)$$

Furthermore, the mean flow rate of air measured at the flowmeter 42 during $T_{resp}$ can be represented as $$\overline{Q_{fm}} = \frac{V_4}{T_{resp}} \qquad (7)$$

where substitution of $V_4$ from Eq. 6 into Eq. 7 yields $$\overline{Q_{fm}} = -\frac{V_2}{T_{resp}} = -\overline{Q_{coll}} \qquad (8)$$

Ohms's law states that in the steady state $$\overline{P_s} = \overline{Q_{coll}} \cdot R_{coll} \qquad (9)$$

where $\overline{P_s}$ represents the mean inflation pressure in the target compartment required to sustain the continuous passage of $\overline{Q_{coll}}$ through the resistive collateral channels represented by $R_{coll}$. Visual inspection of the flow and pressure signals (FIG. 8C) within a single $T_{resp}$ shows that during the inspiratory time, $P_b$ corresponds to $P_s$ since no air can enter or leave the isolated compartment 30 via the catheter's inside lumen 37 during the inspiratory phase. During expiration, however, $P_b = 0$ since it is measured at the valve opening where pressure is atmospheric, while $P_s$ must still overcome the resistive pressure losses produced by the passage of $Q_{fm}$ through the long catheter's inside lumen 37 represented by $R_{saw}$ during the expiratory phase effectively making $\overline{P_s}$ less negative than $\overline{P_b}$ by $\overline{Q_{fm}} \cdot R_{saw}$. Accordingly $$\overline{P_s} = \overline{P_b} + \overline{Q_{fm}} \cdot R_{saw} \qquad (10)$$

and substitution of $P_s$ from Eq. 9 into Eq. 10 results in $$\overline{P_b} = \overline{Q_{coll}} \cdot R_{coll} - \overline{Q_{fm}} \cdot R_{saw} \qquad (11)$$

after subsequently solving for $\overline{P_b}$. Furthermore, substitution of $\overline{Q_{coll}}$ from Eq. 8 into Eq. 11 yields $$\overline{P_b} = -\overline{Q_{fm}} \cdot (R_{coll} + R_{saw}) \qquad (12)$$

and division of Eq. 12 by $\overline{Q_{fm}}$ finally results in $$\frac{\overline{P_b}}{\overline{Q_{fm}}} = -(R_{coll} + R_{saw}) \qquad (13)$$

where the absolute value of Eq. 13 leads back to the aforementioned relation originally stated in Eq. 1.

Figure 9A:
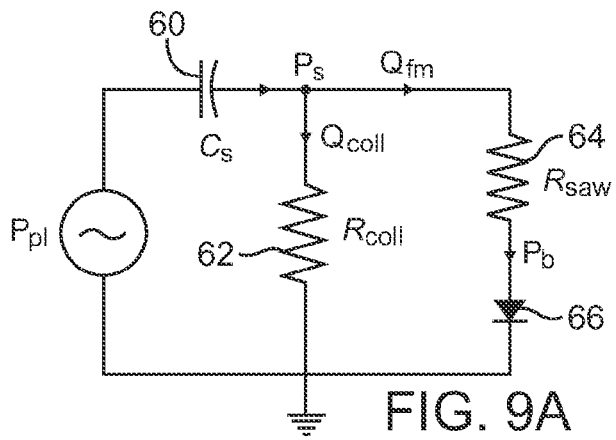
FIGS. 9A-9C illustrate a circuit model representing the system of FIGS. 7A-7B.
Figures 9B, 9C:
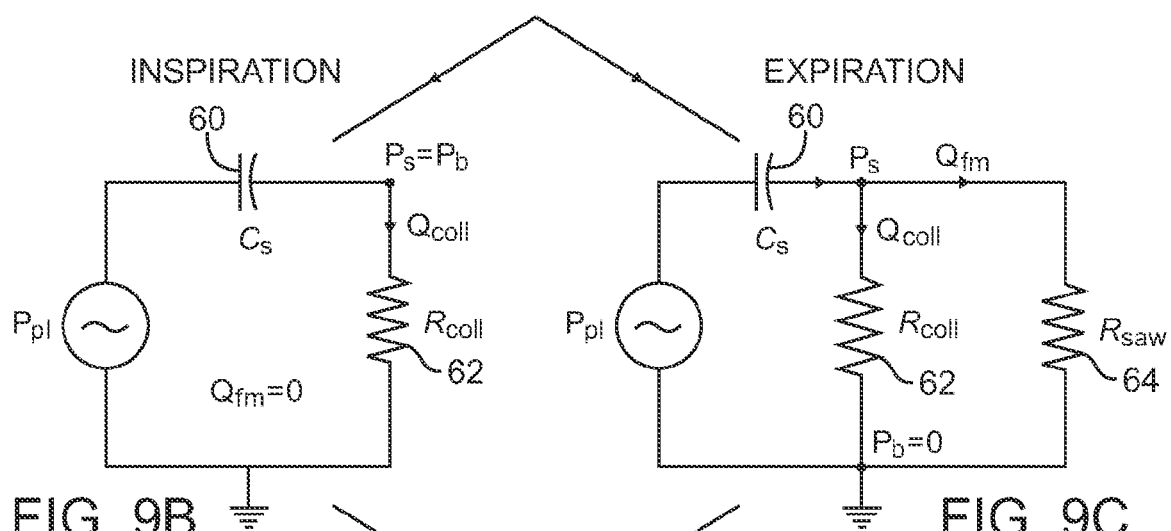

The system illustrated in FIGS. 7A-7B can be represented by a simple circuit model as illustrated in FIGS. 9A-9C. The air storage capacity of the alveoli confined to the isolated compartment 30 representing $C_s$ is designated as a capacitance element 60. The pressure gradient ($P_s-P_b$) from the alveoli to atmosphere via the catheter's inside lumen 37 is caused by the small airways resistance, $R_{saw}$, and is represented by resistor 64. The pressure gradient from the alveoli to atmosphere through the collateral channels is generated by the resistance to collateral flow, $R_{coll}$, and is represented by resistor 62.

Figure 10A:
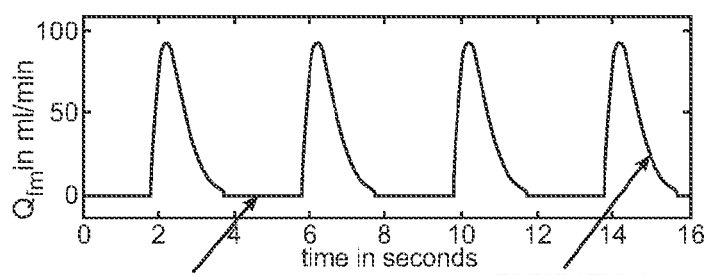
FIGS. 10A-10B illustrate measurements taken from the system of FIGS. 7A-7B.
Figure 10B:
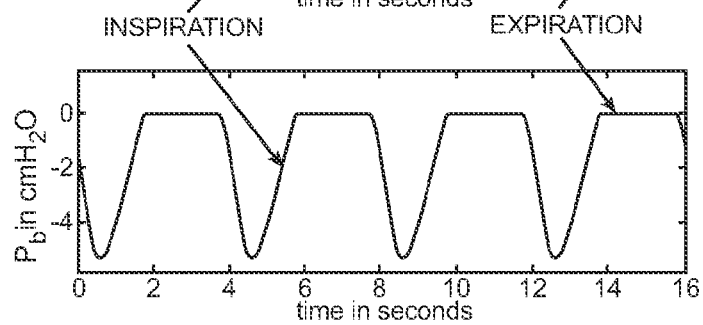

Accordingly, the elasticity of the isolated compartment 30 is responsible for the volume of air obtainable solely across $R_{coll}$ during the inspiratory effort and subsequently delivered back to atmosphere through $R_{saw}$ and $R_{coll}$ during expiration. Pressure changes during respiration are induced by the variable pressure source, $P_{pl}$ representing the varying negative pleural pressure within the thoracic cavity during the respiratory cycle. An ideal diode 66 represents the one-way valve 48, which closes during inspiration and opens during expiration. Consequently, as shown in FIGS. 10A-10B, the flow measured by the flow meter ($Q_{fm}$) is positive during expiration and zero during inspiration, whereas the pressure recorded on the pressure sensor ($P_b$) is negative during inspiration and zero during expiration.

Figures 11A, 11B:
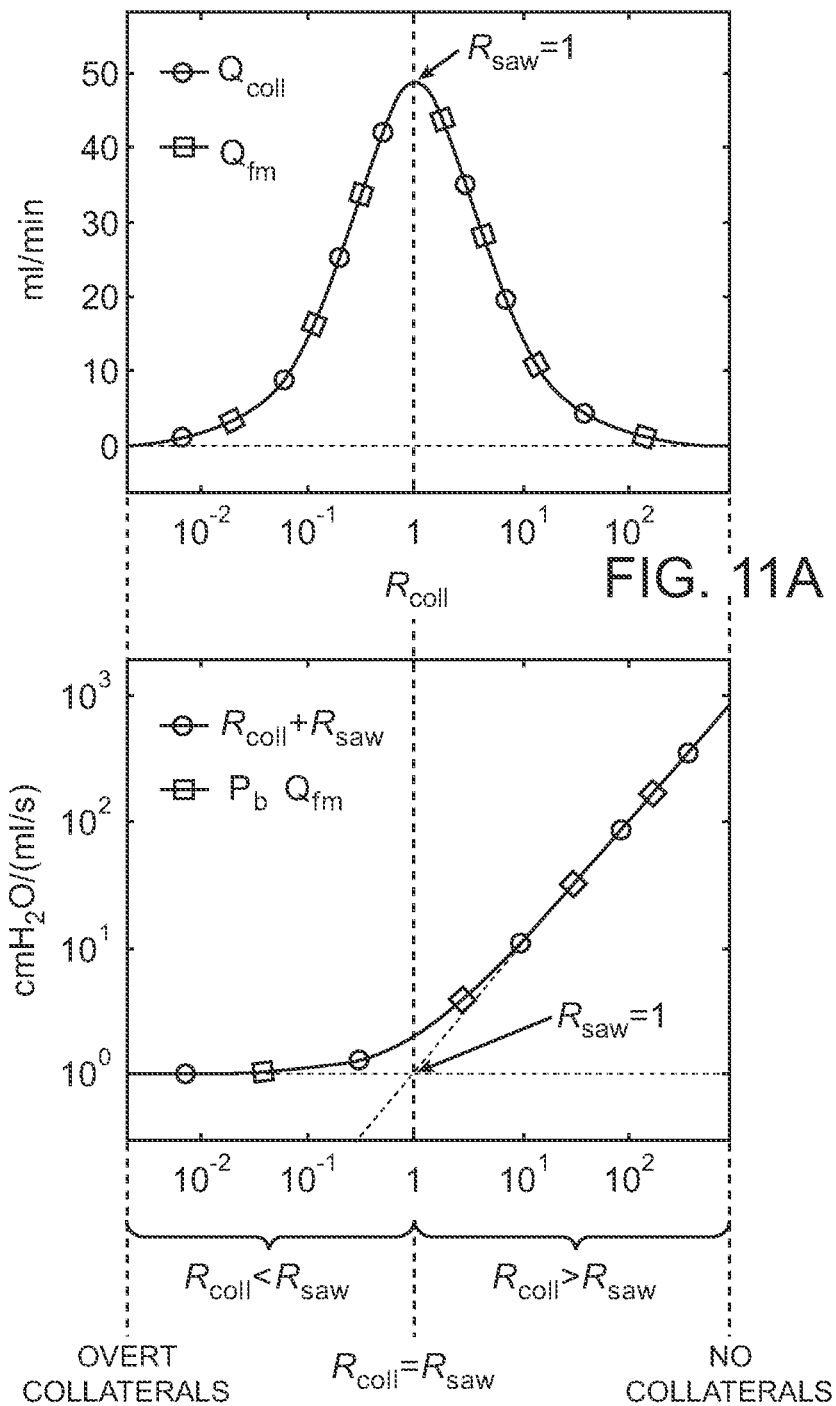
FIGS. 11A-11D illustrate graphical comparisons yielded from the computational model of the collateral system illustrated in FIGS. 7A-7B and FIGS. 9A-9B.
Figure 11C:
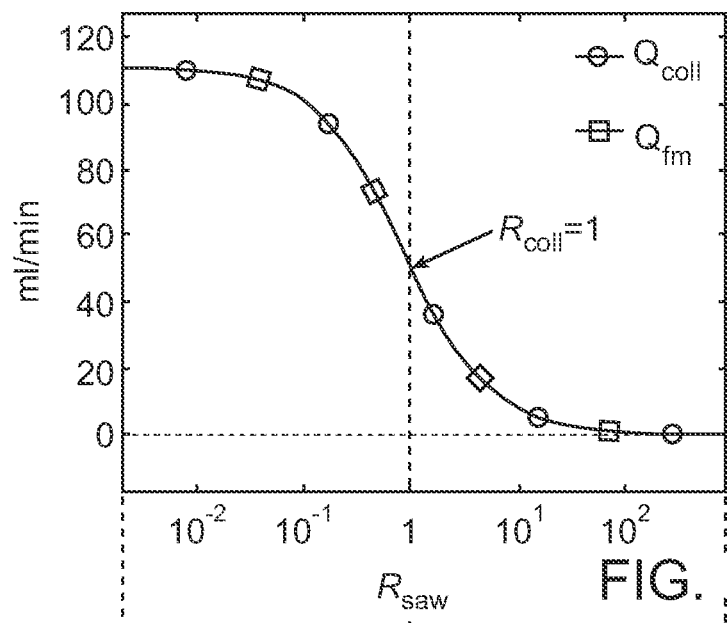

Evaluation of Eqs. 1 & 8 by implementation of a computational model of the collateral system illustrated in FIGS. 7A-7B and FIGS. 9A-9C yields the graphical comparisons presented in FIGS. 11A-11D. FIG. 11A displays the absolute values of mean $Q_{fm}$ ($|\overline{Q_{fm}}|$) and mean $Q_{coll}$ ($|\overline{Q_{coll}}|$) while the FIG. 11B shows the model parameters $R_{coll}+R_{saw}$ plotted together with $|\overline{P_b}/\overline{Q_{coll}}|$ as a function of $R_{coll}$. The values denote independent realizations of computer-generated data produced with different values of $R_{coll}$ while $R_{saw}$ is kept constant at 1 cmH$_2$O/(ml/s). FIG. 11A displays the absolute values of $|\overline{Q_{fm}}|$ and $|\overline{Q_{coll}}|$ while FIG. 11C shows the model parameters $R_{coll}+R_{saw}$ plotted together with $|\overline{P_b}/\overline{Q_{coll}}|$ as a function of $R_{saw}$. The values denote independent realizations of computer-generated data produced with different values of $R_{saw}$ while $R_{coll}$ is kept constant at 1 cmH$_2$O/(ml/s). It becomes quite apparent from FIGS. 11A-11B that the flow is maximal when $R_{coll} \approx R_{saw}$ and diminishes to zero as $R_{coll}$ approaches the limits of either "overt collaterals" or "no collaterals". Accordingly, small measured flow $Q_{fm}$ can mean both, very small and very large collateral channels and hence no clear-cut decision can be made regarding the existence of collateral ventilation unless $R_{coll}+R_{saw}$ is determined as $|\overline{P_b}/\overline{Q_{fm}}|$. The reason for this is that when $R_{coll}$ is very small compared to $R_{saw}$, all gas volume entering the target compartment via the collateral channels leaves via the same pathway and very little gas volume is left to travel to atmosphere via the small airways as the isolated compartment empties. The measured pressure $P_b$, however, changes accordingly and effectively normalizes the flow measurement resulting in an accurate representation of $R_{coll}+R_{saw}$, which is uniquely associated with the size of the collateral channels and the correct degree of collateral ventilation.

Figure 11D:
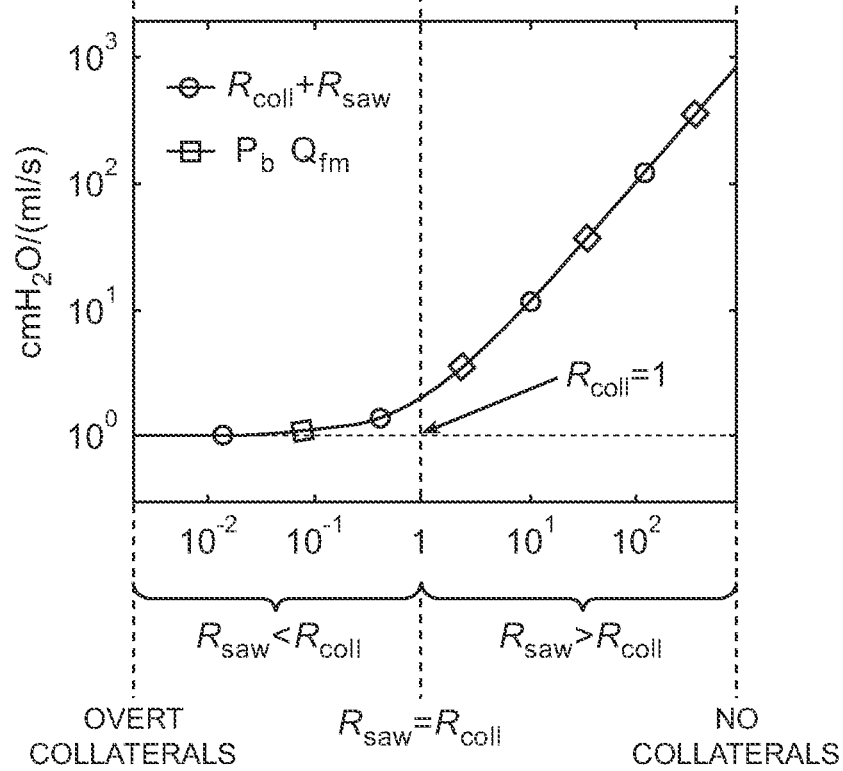

Similarly, FIGS. 11C-11D supplement FIGS. 11A-11B as it shows how the measured flow $Q_{fm}$ continuously diminishes to zero as $R_{saw}$ becomes increasingly greater than $R_{coll}$ and furthermore increases to a maximum, as $R_{saw}$ turns negligible when compared to $R_{coll}$. When $R_{saw}$ is very small compared to $R_{coll}$, practically all gas volume entering the target compartment via the collateral channels travels back to atmosphere through the small airways and very little gas volume is left to return to atmosphere via the collateral channels as the isolated compartment empties. Thus, determination of $|\overline{P_b}/\overline{Q_{fm}}|$ results in an accurate representation of $R_{coll}+R_{saw}$ regardless of the underlying relation amongst $R_{coll}$ and $R_{saw}$. In a healthy human, resistance through collateral communications, hence $R_{coll}$, supplying a sublobar portion of the lung is many times (10-100 times) as great as the resistance through the airways supplying that portion, $R_{saw}$ (Inners 1979, Smith 1979, Hantos 1997, Suki 2000). Thus in the normal individual, $R_{coll}$ far exceeds $R_{saw}$ and little tendency for collateral flow is expected. In disease, however, this may not be the case (Hogg 1969, Terry 1978). In emphysema, $R_{saw}$ could exceed $R_{coll}$ causing air to flow preferentially through collateral pathways.

Therefore, the above described models and mathematical relationships can be used to provide a method which indicates the degree of collateral ventilation of the target lung compartment of a patient, such as generating an assessment of low, medium or high degree of collateral ventilation or a determination of collateral ventilation above or below a clinical threshold. In some embodiments, the method also quantifies the degree of collateral ventilation, such generating a value which represents $R_{coll}$. Such a resistance value indicates the geometric size of the collateral channels in total for the lung compartment. Based on Poiseuille's Law with the assumption of laminar flow, $$R \propto (\eta \times L)/r^4 \tag{14}$$

wherein $\eta$ represents the viscosity of air, L represents the length of the collateral channels and r represents the radius of the collateral channels. The fourth power dependence upon radius allows an indication of the geometric space subject to collateral ventilation regardless of the length of the collateral channels.

Figure 12A:
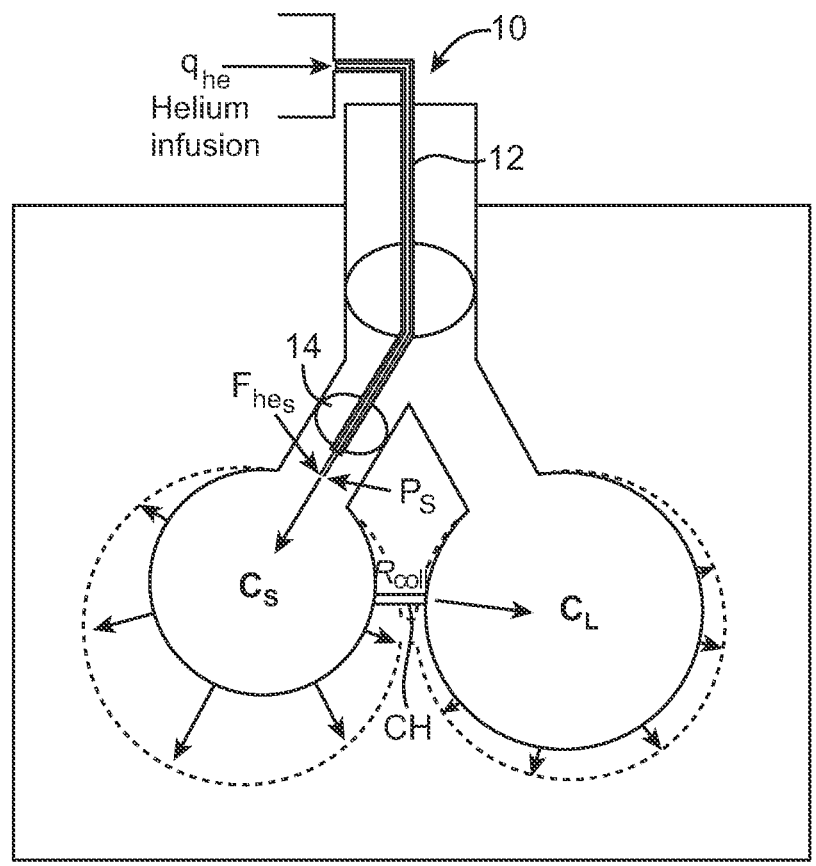
FIG. 12A illustrates a two-compartment model which is used to generate a method quantifying the degree of collateral ventilation.
Figure 12B:
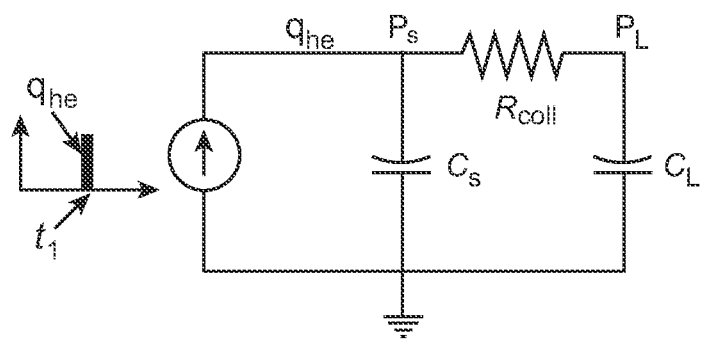
FIG. 12B illustrates an electrical circuit analog model.

FIG. 12A illustrates a two-compartment model which is used to generate a method quantifying the degree of collateral ventilation, including a) determining the resistance to segmental collateral flow $R_{coll}$, b) determining the state of segmental compliance $C_s$, and c) determining the degree of segmental hyperinflation $q_s$. Again, $C_s$ characterizes the compliance of the target compartment or segment. $C_L$ represents the compliance of the rest of the lobe. $R_{coll}$ describes the resistance to the collateral airflow. FIG. 12B provides an electrical circuit analog model. In this example, at time t=$t_1$, approximately 5-10 ml of 100% inert gas such as He ($q_{he}$) is infused. After a period of time, such as one minute, the pressure ($P_S$) & the fraction of He ($F_{he_S}$) are measured.

The dynamic behavior of the system depicted in FIGS. 12A-12B can be described by the time constant $\tau_{coll}$ $$t_{coll} = R_{coll} \cdot \underbrace{\frac{C_S C_L}{C_S + C_L}}_{C_{eff}} \tag{15}$$

Figure 12C:
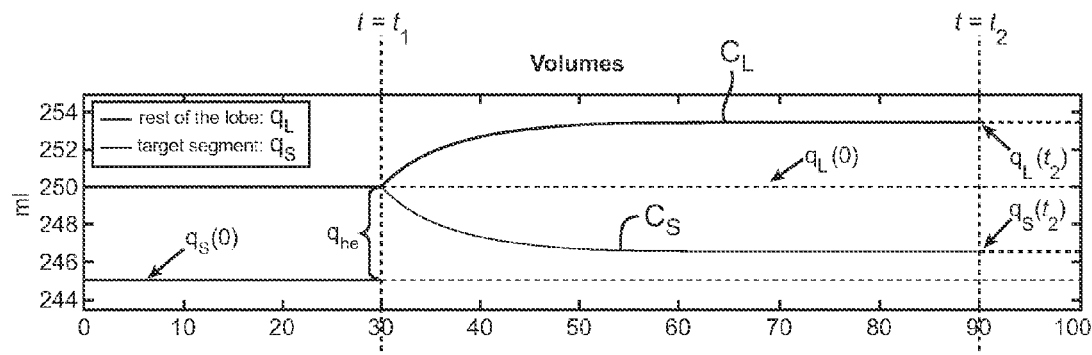
FIGS. 12C-12E illustrate the resulting time changes in volumes, pressures and gas concentrations in the target compartment and the rest of the lobe.
Figure 12D:
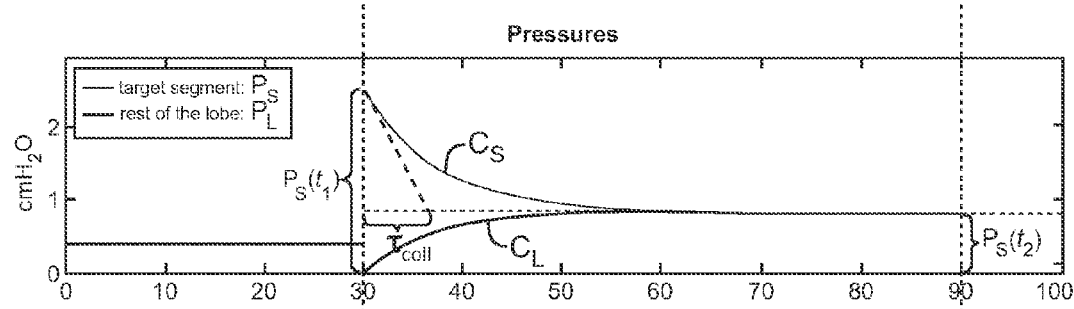
Figure 12E:
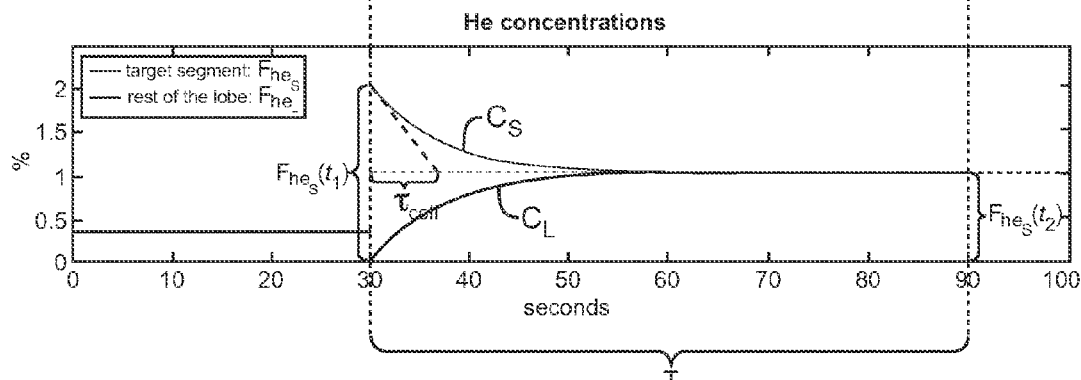

At time $t_1$=30 s, a known fixed amount of inert gas ($q_{he}$: 5-10 ml of 100% He) is rapidly injected into the target compartment $C_s$, while the rest of the lobe remains occluded, and the pressure ($P_S$) and the fraction of He ($F_{he_S}$) are measured in the target segment for approximately one minute (T=60 s). FIGS. 12C-12E illustrate the resulting time changes in volumes, pressures and gas concentrations in the target compartment $C_s$ and the rest of the lobe $C_L$. Eqs. 16-21 state the mathematical representation of the lung volumes, pressures and gas concentrations at two discrete points in time, $t_1$ and $t_2$.

$$q_s(t_1) = q_s(0) + q_{he} \tag{16}$$

$$q_s(t_2) + q_L(t_2) = q_s(0) + q_L(0) + q_{he} \tag{17}$$

$$P_s(t_1) = \frac{q_{he}}{C_s} \quad (18)$$

$$P_s(t_2) = \frac{q_{he}}{(C_s + C_L)} \quad (19)$$

$$F_{he_s}(t_1) = \frac{q_{he}}{q_s(t_1)} \quad (20)$$

$$F_{he_s}(t_2) = \frac{q_{he}}{q_s(t_1) + q_L(t_2)} \quad (21)$$

As a result, the following methods may be performed for each compartment or segment independently: 1) Assess the degree of segmental hyperinflation, 2) Determine the state of segmental compliance, 3) Evaluate the extent of segmental collateral communications.

Segmental Hyperinflation

The degree of hyperinflation in the target segment, $q_S(0)$, can be determined by solving Eq. 16 for $q_S(0)$ and subsequently substituting $q_S(t_1)$ from Eq. 20 into Eq. 16 after appropriate solution of Eq. 20 for $q_S(t_1)$ as $$q_S(0) = q_{he} \cdot \left( \frac{1 - F_{he_s}(t_1)}{F_{he_s}(t_1)} \right) \quad (22)$$

Segmental Compliance

The state of compliance in the target segment, $C_S$, can be determined simply by solving Eq. 18 for $C_S$ as $$C_S = \frac{q_{be}}{P_S(t_1)} \quad (23)$$

Segmental Collateral Resistance

A direct method for the quantitative determination of collateral system resistance in lungs, has been described above. Whereas, the calculation below offers an indirect way of determining segmental collateral resistance.

The compliance of the rest of the lobe, $C_L$, can be determined by solving Eq. 19 for $C_L$ and subsequently substituting $C_S$ with Eq. 23. Accordingly $$C_L = q_{he} \cdot \frac{P_S(t_1) - P_S(t_2)}{P_S(t_1) P_S(t_2)} \quad (24)$$

As a result, the resistance to collateral flow/ventilation can alternatively be found by solving Eq. 15 for $R_{coll}$ and subsequent substitution into Eq. 15 of $C_S$ from Eq. 24 and $C_L$ from Eq. 25 as $$R_{coll} = \frac{\tau_{coll}}{C_{eff}} \quad (25)$$

where $C_{eff}$ is the effective compliance as defined in Eq. 15.
Additional Useful Calculation for Check and Balances of all Volumes The degree of hyperinflation in the rest of the lobe, hence $q_L(0)$, can be determined by solving Eq. 17 for $q_L(0)$ and subsequently substituting $q_S(t_2)+q_L(t_2)$ from Eq. 21 into Eq. 17 after appropriate solution of Eq. 21 for $q_S(t_2)+q_L(t_2)$. Thus $$q_L(0) = q_{he} \cdot \left( \frac{F_{he_s}(t_1) - F_{he_s}(t_2)}{F_{he_s}(t_1) F_{he_s}(t_2)} \right) \quad (26)$$

Equation 26 provides an additional measurement for check and balances of all volumes at the end of the clinical procedure.

Regardless of the method of quantifying collateral ventilation, the magnitude of collateral ventilation is dependent on the patient's respiratory mechanics. For instance, a patient that is breathing very shallow at −2 cmH$_2$O of pleural pressure creates a minimal amount of lung compartment expansion and hence the collateral channels remain somewhat resistive. The measured collateral ventilation will therefore be correspondingly low. Conversely, if a patient is breathing deep at −10 cmH$_2$O of pleural pressure, a lot of lung expansion takes place which stretches the effective cross-sectional area of the collateral channels and hence the collateral channels become less resistive to flow resulting in a commensurate increase in collateral ventilation (references where Rcoll=f (V) as in Woolcock's 1971 or Inners' 1979, and references with and Rcoll=f(P) as in Robinson's 1978 and Olsen's 1986). Even in the ideal situation where the resistance to collateral channels remains independent of effort, greater effort translates into greater airflow (Baker's 1969 paper).

Figure 13A:
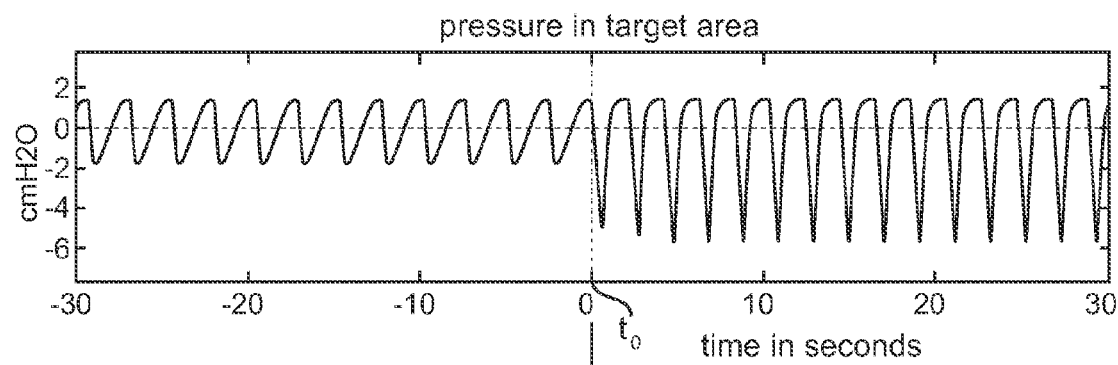
FIGS. 13A-13C illustrate changes in measured variables based on degree of effort.
Figure 13B:
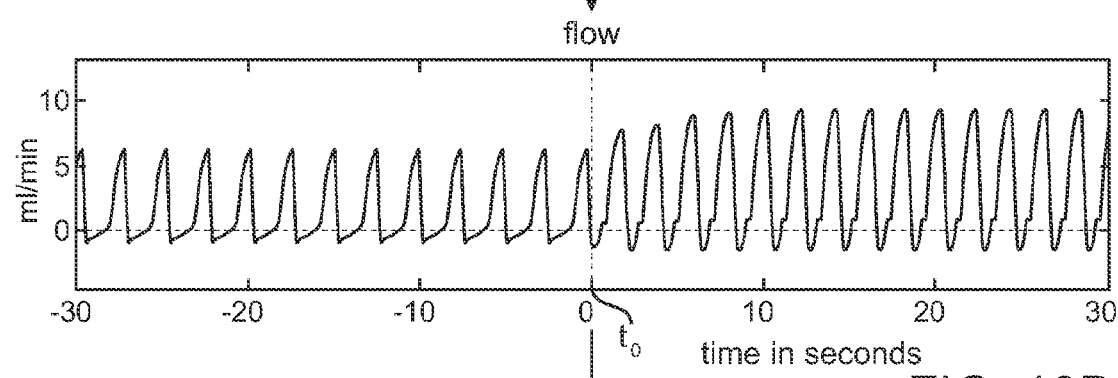
Figure 13C:
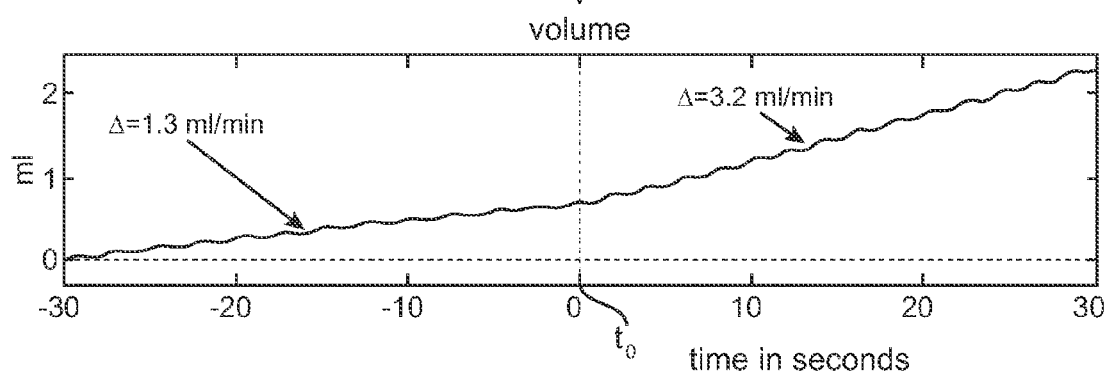

Therefore, an aspect of the present invention includes measuring the patient breathing effort so that the collateral ventilation measurement can be calculated as a function of the degree and/or frequency of that effort, in effect normalizing the measurement to any situation. The breathing effort can be measured in terms of tidal volume inspired by the patient, or by inspiratory flow rate, peak inspiratory flow rate, pleural pressure created (for example as measured by an esophageal pressure transducer), upper airway pressure, work-of-breathing in joules of energy exerted per liter of air inspired, thoracic cavity expansion (such as measured by chest wall expansion) or other means. FIGS. 13A-13C illustrate changes in measured variables based on degree of effort, i.e. during shallow and deep breathing. For example, FIG. 13A illustrates pressure measurements in a target lung compartment. At t=0 ($t_0$), there is a change in respiratory effort so that the depth of inspiration is increased. Consequently the amplitude of the pressure wave is increased. Similarly, referring to FIG. 13B, the corresponding volumetric flow rate wave also increases in amplitude at t=0 ($t_0$) with a larger mean flow rate leaving the target lung compartment as a result. And, referring to FIG. 13C, the volume leaving the target lung compartment and accumulated over time, such as within a specialized container, may be calculated by integration of the volumetric flow rate data from FIG. 13B. As shown, the slope of the volume curve changes at t=0 ($t_0$). The slope denoting the change in volume over time corresponds to the mean flow rate.

In some embodiments, a specially configured breathing effort sensor is provided. Such sensors include but are not limited to a mouthpiece that allows for simultaneous passage through the mouth of the isolation catheter 10 and measurement of airflow through the mouthpiece (around the outside of the catheter shaft).

Figure 14A:
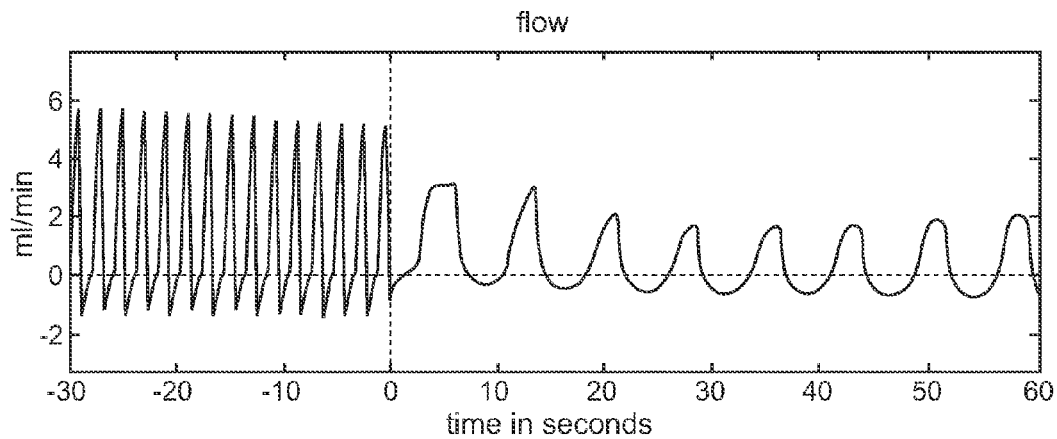
FIGS. 14A-14B illustrate changes in measured variables based on frequency of effort.
Figure 14B:
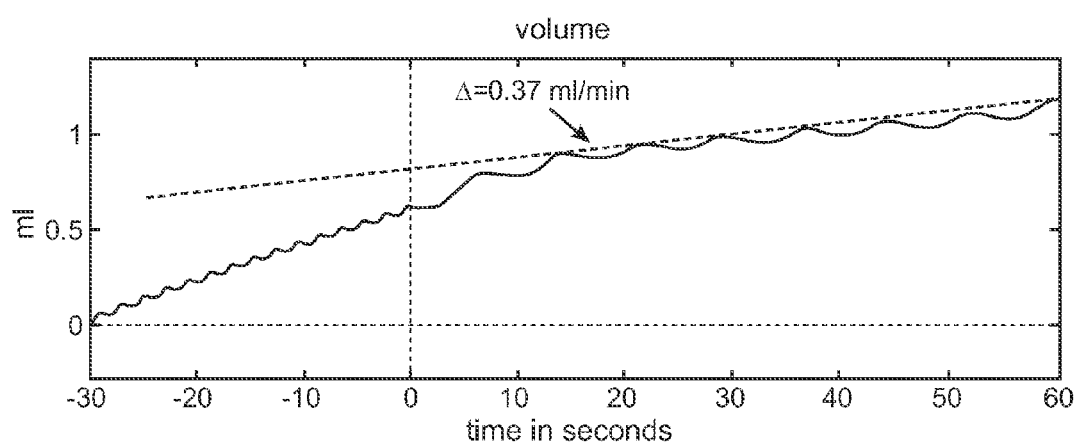

FIGS. 14A-14B illustrate changes in measured variables based on frequency of effort, i.e. during fast and slow breathing. For example, FIG. 14A illustrates volumetric flow rate measurements in a target lung compartment. At t=0 ($t_0$), there is a change in respiratory frequency so that the frequency of respiration is decreased or slowed down resulting in a smaller mean flow rate leaving the target lung compartment. Similarly, referring to FIG. 14B, the volume accumulated over time, such as within a specialized container, may be calculated by integration of the volumetric flow rate data from FIG. 14A. As shown, the slope of the volume curve changes at t=0 ($t_0$) indicating smaller volumetric increases per breath. The slope denoting the change in volume over time corresponds to the mean flow rate.

The units of measure of the collateral ventilation variable, which takes into account the degree and/or frequency of the involved respiratory effort, are therefore reported in units of A/B where A is the measurement of collateral ventilation and B is the measurement of respiratory drive. The result of the normalized collateral ventilation variable can be reported, for example, as but not limited to an average, a peak value or a range. Thus, it should be recognized that the desired measurement and reporting of the collateral ventilation normalized result includes a mathematical relation and in its most convenient form, a system and the necessary devices to acquire all the needed measured parameters in a single instrument to apply the said mathematical relation to perform the calculation.

It should be appreciated that the normalization technique subject to this invention is independent of the exact collateral ventilation measurement method; any collateral ventilation measurement method can be used with this novel normalization technique.

Figure 15:
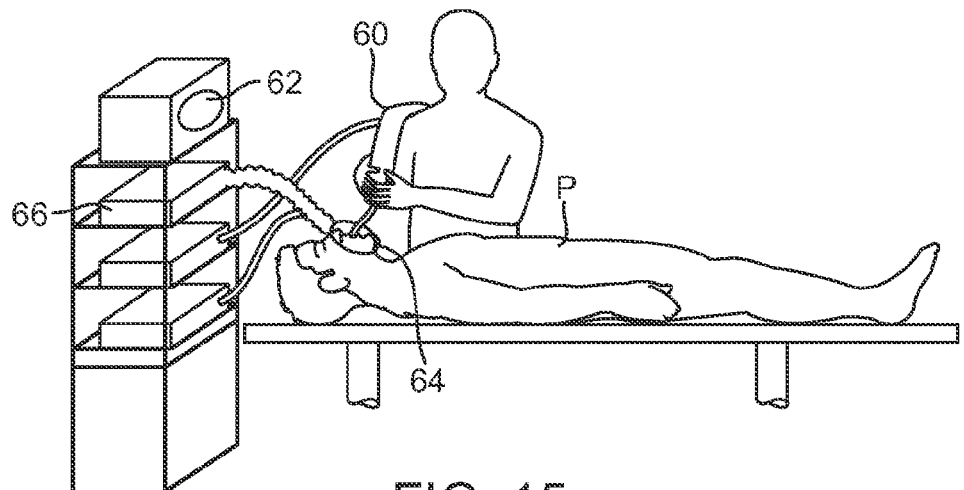
FIGS. 15, 16A-16B illustrate the use of continuous positive airway pressure to assist in the detection of collateral ventilation.

In some embodiments, detection of collateral ventilation is assisted with the application of medically safe continuous positive airway pressure (CPAP), as illustrated in FIG. 15. As shown, the targeted lung compartment is isolated as previously described with the placement of an isolation catheter into the targeted lung compartment of the patient P. In this embodiment, the isolation catheter is placed with the use of a bronchoscope 60 providing an endoscopic view with the use of a monitor 62. CPAP is administered via a nasal or oral-nasal non-invasive mask 64, positionable over the patient's face, which is connected to a CPAP ventilator 66. This specially configured mask 64 simultaneously allows for the administration of CPAP, the passage of the isolation catheter, and optionally breath sensors to measure breathing effort. The isolated target lung compartment is not subjected directly to CPAP, however if collateral channels are present, the detection of these channels is facilitated because the CPAP amplifies the degree of airflow across the channels due to simple pressure gradient laws. Further hyperinflation due to air trapping is prevented using safe pressure levels and I:E ratios. Therefore, CPAP increases the measurement sensitivity of the collateral ventilation measurement technique of using an externally placed but communicating flow meter or special container.

Figure 16A:
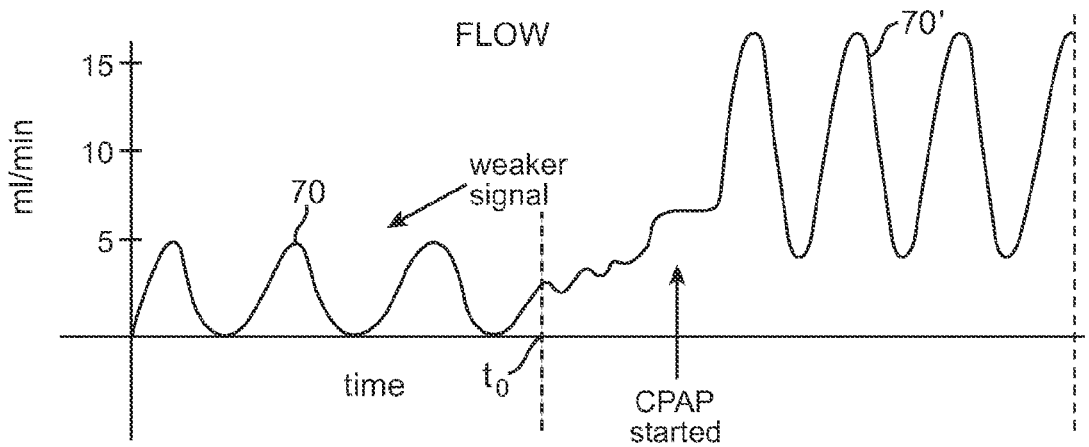
Figure 16B:
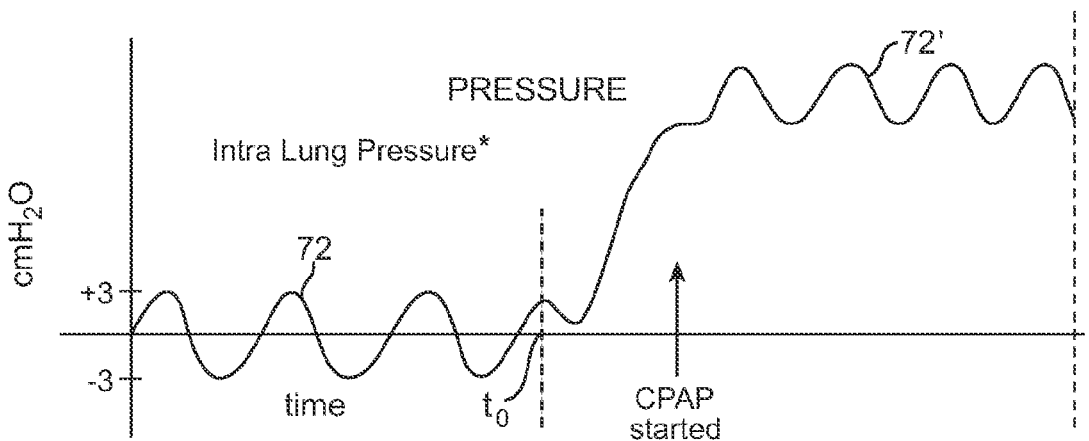

FIG. 16A illustrates example collateral flow measurements recorded by a flow meter. At t=0 ($t_0$), the CPAP mask is positioned on the patient and shortly thereafter CPAP is started resulting in an amplified signal. Thus, prior to t=0 ($t_0$) the flow signal 70 is relatively weak showing spontaneous breathing without CPAP. After t=0 ($t_0$), the flow signal 70' is stronger showing an amplification of the flow rate signal due to CPAP. Similarly, FIG. 16B illustrates example pressure measurements taken in lung compartments that are not isolated by the isolation catheter (the pressure in the isolated lung compartment is less, closer to normal). At t=0 ($t_0$), the CPAP mask is positioned on the patient and shortly thereafter CPAP is started resulting in an amplified signal. Thus, prior to t=0 ($t_0$) the pressure signal 72 is relatively weak showing spontaneous breathing without CPAP. After t=0 ($t_0$), the pressure signal 72' is stronger showing an amplification of the pressure signal due to CPAP.

Figure 17:
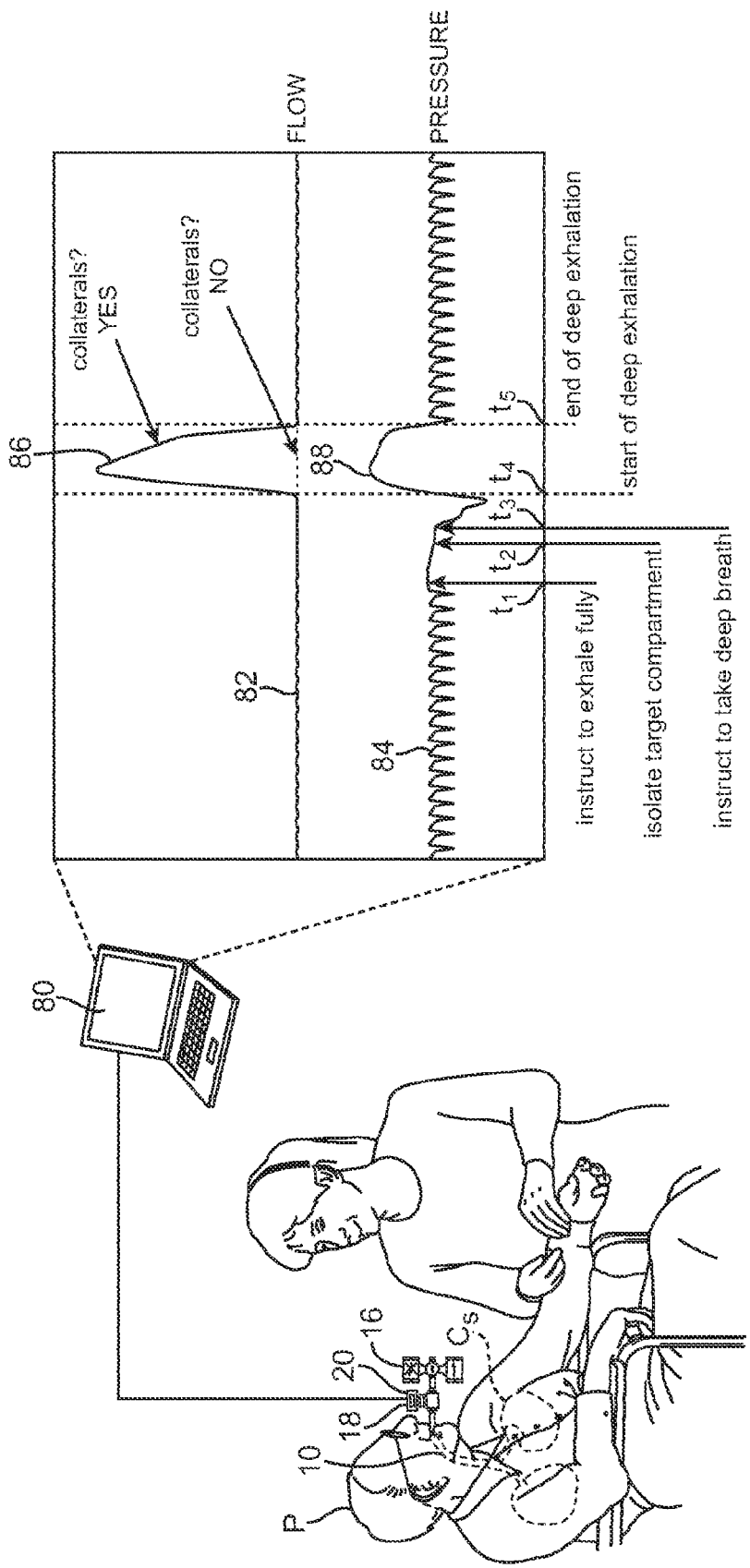
FIG. 17 illustrates a single breath technique.

In some embodiments, a single breath technique is used wherein the collateral ventilation and, if so measured, the patient's breathing effort, are measured for a single breath. Referring to FIG. 17, the targeted lung compartment $C_s$ is cannulated and isolated with an externally communicating catheter 10 as previously described. Here, the patient P is shown having the catheter 10 advanced into the targeted lung compartment $C_s$ and the flowmeter 18 and/or pressure sensor 20 and one-way valve 16 residing outside of his mouth. The flowmeter 18 and/or pressure sensor 20 is linked to a computer 80 which acquires the appropriate data. Example flow rate 82 and pressure curves 84 are shown. The cooperative patient P is instructed to breath out as much air as possible with a forced and extended exhalation effort ($t_1$), and at the end of exhalation (which is detectable with the breath sensing devices) the target lung compartment $C_s$ is isolated ($t_2$). The patient then initiates a maximal inspiratory effort ($t_3$) and starts a deep exhalation ($t_4$) which then ends at ($t_5$). It is presumed that any air exiting the isolation catheter 10 during the deep exhalation ($t_4$-$t_5$) would be from collateral ventilation. If collaterals were present, a flow peak 86 and a pressure peak 88.

The collateral ventilation (and breathing effort if so measured) can be measured and reported as a function of a single breath peak inspiratory effort. Results can be reported normalized or unnormalized for the complete breath, a peak value during the breath, an average value during the breath, the value during a portion of the breath, for example but not limited to the first one second of the breath, an average value of a number of separate single breath measurements or maneuvers. The processing unit in the case of this embodiment includes the requisite algorithms and control systems to obtain and process the measurement as needed.

Figure 18A:
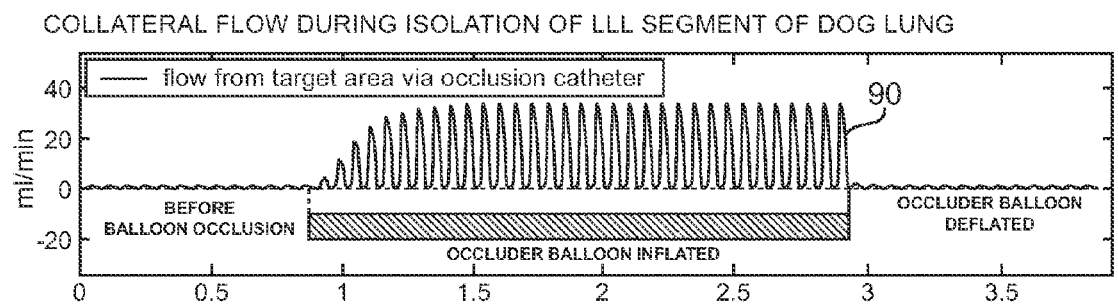
FIGS. 18A-18C illustrate example flow, volume and pressure measurement curves respectively.
Figure 18B:
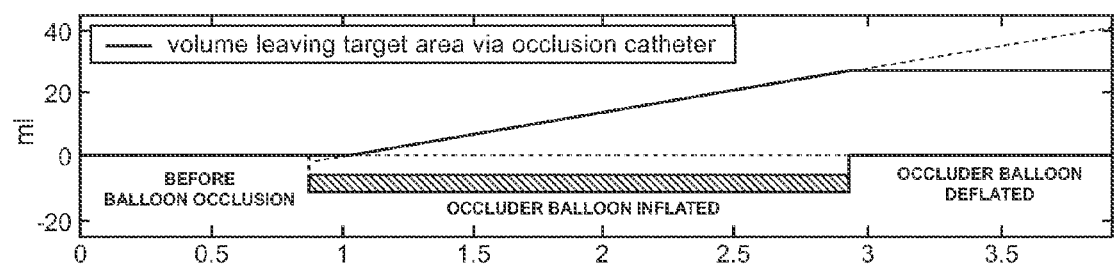
Figure 18C:
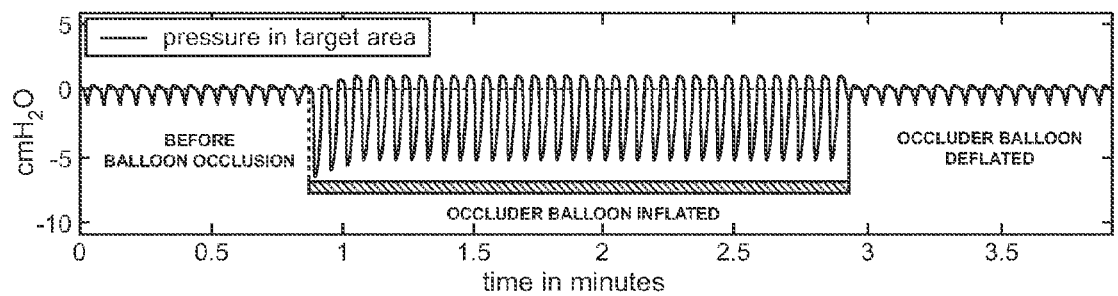

In additional embodiments, airflow measurements are made both before, during and after isolation of the targeted lung compartment $C_s$, wherein such measurements are analyzed to evaluate collateral ventilation. For example, an external flow measuring device is configured to measure flow into and out of a targeted lung compartment $C_s$ via an externally communicating catheter 10 placed into the compartment $C_s$, as previously described. First, the compartment $C_s$ is cannulated with the catheter 10, but without isolating the bronchus. Referring to FIG. 18A, the flow measurement through the catheter lumen is made, resulting in a flowrate curve 90 at baseline. Second, while the flow measurement continues, the bronchus is isolated by inflating the occluder balloon and the amplitude of the flowrate curve 90 increases if there is collateral flow. Then, while the flow measurement continues, the occluder balloon is deflated and the flowrate curve 90 decreases back to baseline. Corresponding volume and pressure measurement curves are shown in FIG. 18B and FIG. 18C respectively. Comparison of the airflow magnitude and direction as measured at the external flow-sensing device provides additional information about the collateral channels in the target compartment and/or verification of the system's integrity. For example, comparison of the amplitudes before and after isolation can also be used to quantify/or normalize the degree of flow via collateral channels and/or check for adequate isolation of the target compartment. This aspect of the invention includes the requisite systems and devices for processing the pre and post airflow measurements and may include an automatic isolation system controlled by instrumentation embedded in the processing unit.

Figure 19:
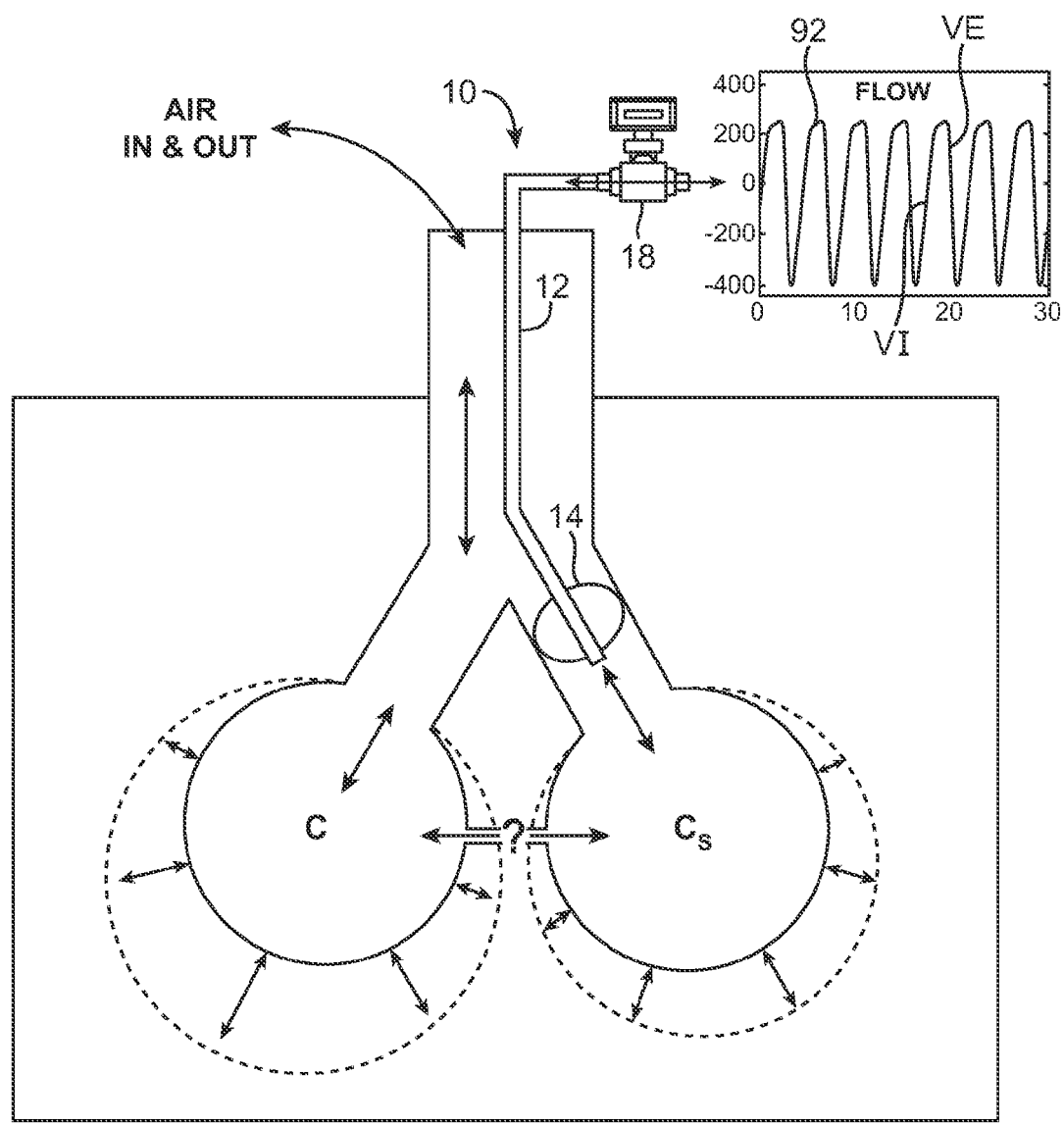
FIG. 19 illustrates flow measured via a catheter wherein differences in the waveform characteristic of inspiration versus exhalation facilitate determining whether collateral ventilation exists.

In an additional embodiment of the present invention, as illustrated in FIG. 19, flow is measured via a catheter 10 as previously described. The occlusion member 14 is positioned and inflated to isolate the target lung compartment $C_s$. As the patient breathes, both the target lung compartment $C_s$ and the non-target compartment C expand and recoil as shown. The measured flow data 92 is closely inspected to compare the waveforms obtained during inspiration and exhalation (inhalation waveform=VI, exhalation waveform=VE). The ratio VI/VE in the presence of collateral ventilation differs from the ratio VI/VE in the absence of collateral ventilation. These and other differences in the waveform characteristics of inspiration versus exhalation shall facilitate determining whether collateral ventilation exists.

Figure 20A:
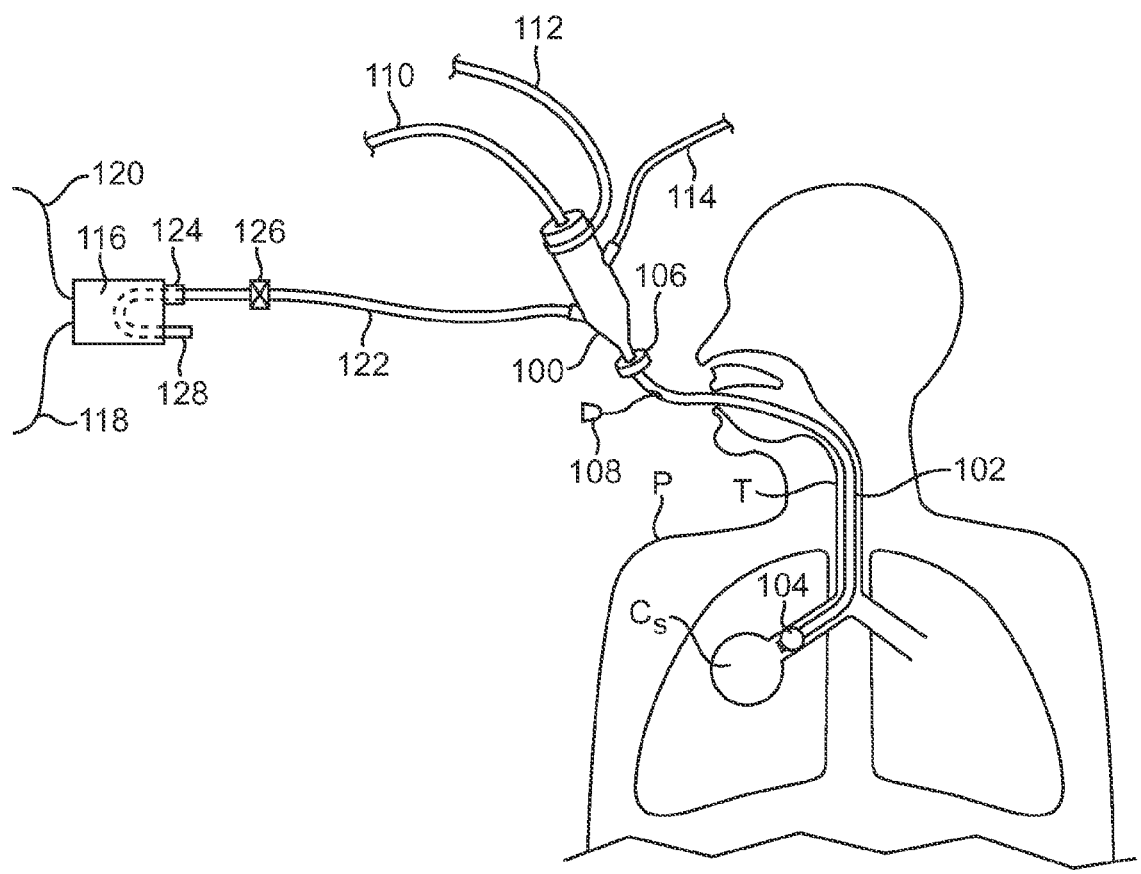
FIGS. 20A-20B illustrate an embodiment of an isolation catheter including a bronchoscope.
Figure 20B:
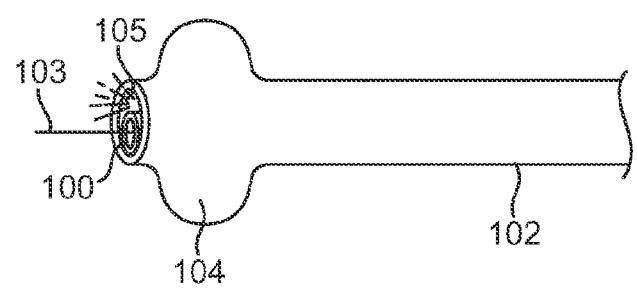

In some embodiments, as illustrated in FIGS. 20A-20B, the isolation catheter 10 includes a fiberoptic endoscope, or bronchoscope 100, with optional built-in imaging, illumination and/or steering. FIG. 20A illustrates the bronchoscope 100 inserted into an external sheath 102 having an occlusion member 104 and joined at a sheath proximal connector 106. Exemplary embodiments of suitable external sheaths having inflation cuffs for use with bronchoscopes or other endoscopic instruments are described in U.S. Pat. No. 6,585,639, incorporated herein by reference for all purposes. FIG. 20B provides a more detailed illustration of the distal end of the bronchoscope 100 and sheath 102 of FIG. 20A. Thus, a working channel 103 of the bronchoscope 100 is shown along with imaging features 105. Referring back to FIG. 20A, the bronchoscope 100 and sheath 102 are advanced down the trachea T of the patient P to the target lung compartment $C_s$ so that the inflation cuff 104 is positioned to isolate the target lung compartment $C_s$. The sheath 102 also includes a cuff inflation line/valve 108 which can be used to measure cuff pressure. The bronchoscope 100 includes an imaging cable 110 and light cable 112, as shown. Optionally, a suction line 114 may also be connected with the bronchoscope 100. The shaft of the bronchoscope includes a lumen extending most of its length to which a flow-measuring device 116 is connected external to the patient P. As shown, the flow-measuring device 116 has a power cord 118 and a signal to main processor 120. Tubing 122 connects the bronchoscope 100 to an inlet 124 of the flow-measuring device 110, wherein a check valve 126 is present along the tubing 122. Air, gasses or other measured entities are released from the flow-measuring device 116 via an outlet 128. The sheath 102 or an outer sleeve may be equipped with additional lumens that extend across the occlusion member 104 for the purpose of measuring flow or other respiratory or physiological parameters, or for delivering agents or tracer gases.

Figure 21A:
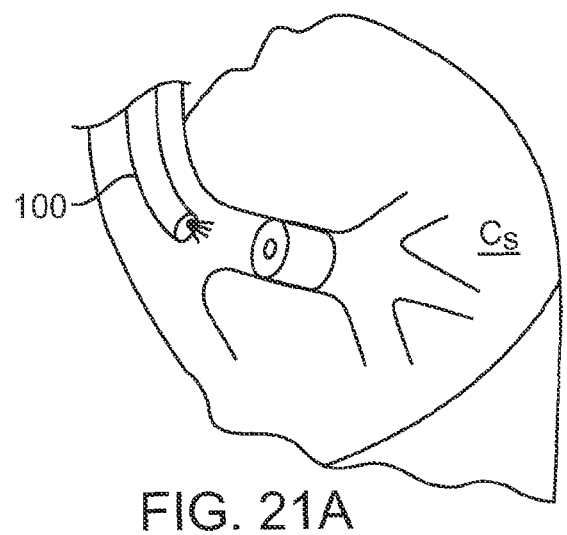
FIGS. 21A-21C illustrate the performance of a collateral ventilation test through an occlusal stent.
Figure 21B:
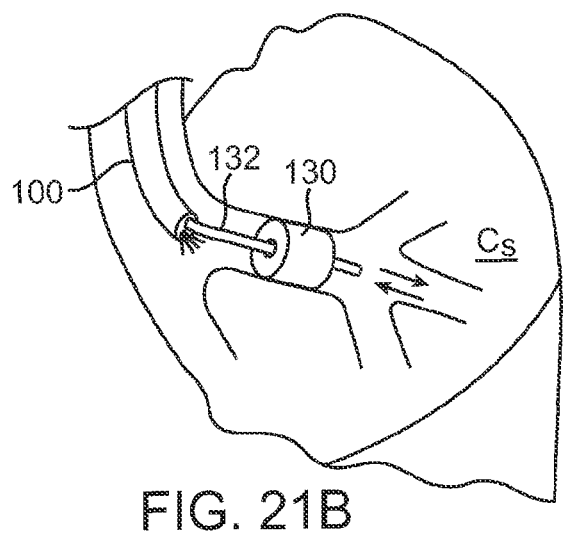
Figure 21C:
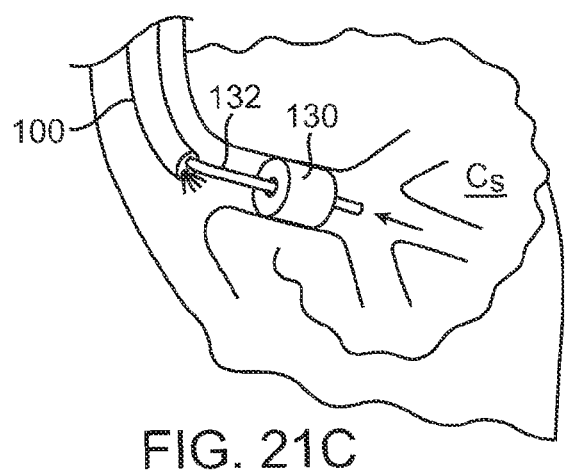

Alternatively, in the absence of a sheath 102 having an occlusion member 104, a special catheter may be inserted into the lumen of the bronchoscope 100 and can be used to access the targeted lung compartment $C_s$. The catheter may to create the isolation seal by any appropriate means, including creating an isolation seal with an inflatable element mounted on the distal end of the catheter or by connecting with or passing through an occlusal stent which is positioned to seal the bronchial lumen. For example, FIGS. 21A-21C illustrate the performance of a collateral ventilation test through an occlusal stent 130. Referring to FIG. 21A, an occlusal stent 130 is shown sealing a bronchial lumen leading to a target lumen compartment $C_s$. A bronchoscope 100 is shown advanced to a position near the occlusal stent 130. Referring to FIG. 21B, a catheter 132 is advanced through the bronchoscope 100 and through the occlusal stent 130, accessing the target lung compartment $C_s$. The occlusal stent 130 includes a valve which allows the catheter 132 to advance therethrough while maintaining isolation of the target lung compartment $C_s$. Measurements of pressure, flow or other respiratory or physiological parameters are then taken, with or without a one-way valve and/or external special container, either at the tip of the catheter 132 in the targeted lung compartment $C_s$ or at the proximal end of the catheter 132, external to the patient, through a lumen in the catheter 132 that extends the catheter's length. When accessing through an occlusal stent 130, volume reduction therapy may then be performed by aspirating through the catheter 132 and stent 132, as illustrated in FIG. 21C. The catheter 132 is then removed and the volume reduction maintained.

In a similar but further embodiment, gas temperature is measured at some point along the catheter lumen either instead of the flow rate measurement or to complement the flow rate measurement, in order to further interpret the data being collected and/or to further distinguish between expiratory flow and inspiratory flow through the catheter lumen.

Figure 22A:
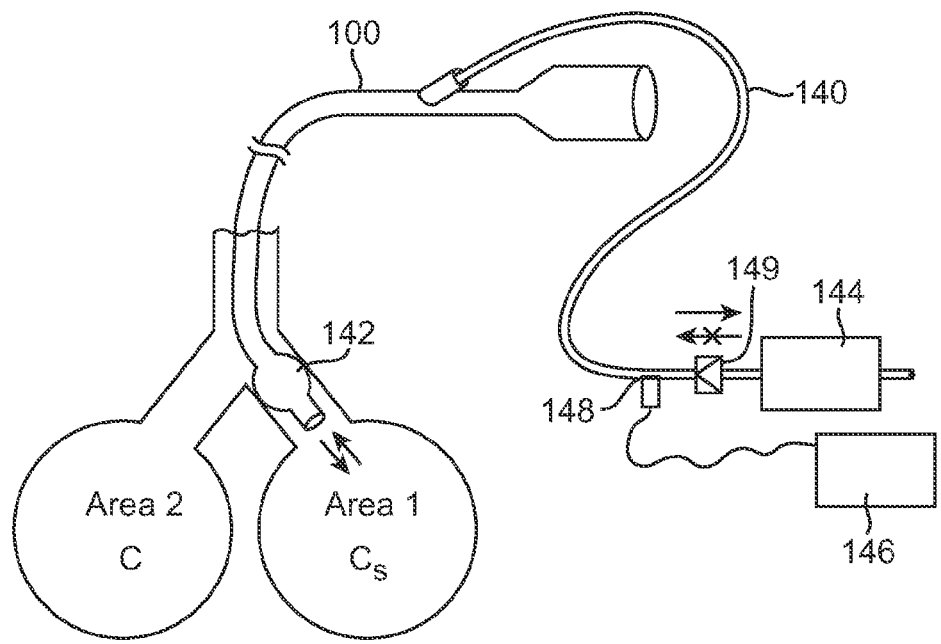
FIGS. 22A-22C illustrate the use of carbon dioxide to indicate collateral flow.
Figure 22B:
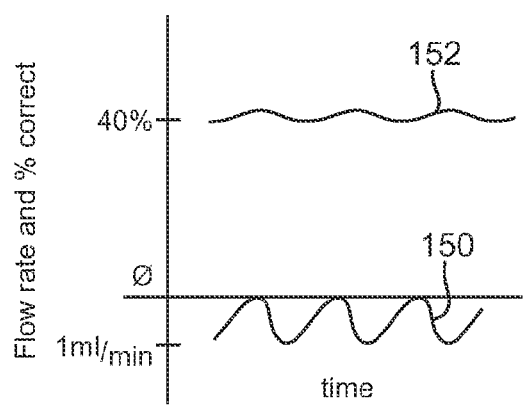
Figure 22C:
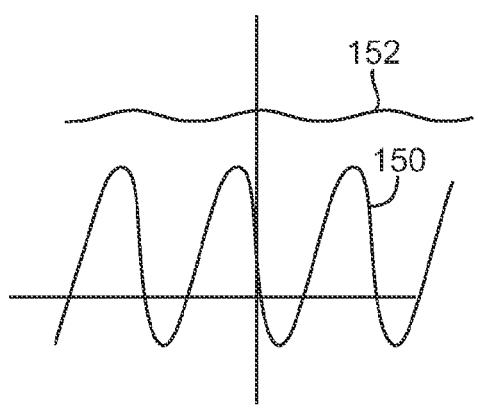

In a still further embodiment of the present invention, respiratory gas composition of the target lung compartment $C_s$ is measured to facilitate further interpretation of the airflow data gathered by a flow measuring device. Such measurement may be taken separately or simultaneously with the flow rate measurements. For example, a certain decay rate of $O_2$ composition in the gas at the external end of the catheter may be indicative of no or little collateral flow, whereas a slower or no decay rate of $O_2$ may be indicative of collateral flow since fresh oxygen inspired by the patient can enter the target compartment $C_s$ via the collateral channels. Other gases, for example $CO_2$, can also be measured, as illustrated in FIGS. 22A-22C. FIG. 22A illustrates a catheter 140 advanced through a bronchoscope 100 having an occlusion member 142 which seals a bronchial lumen leading to a target lumen compartment $C_s$. The catheter 140 is connected with a flow sensing device 144, as described above. In addition, the catheter 140 is connected with a gas sensing device 146, such as a capnographer, having a gas sensor 148. Measurements of flow or other respiratory or physiological parameters are then taken, with or without a one-way valve 149 and/or external special container, either at the tip of the catheter 140 in the targeted lung compartment $C_s$ or at the proximal end of the catheter 140, external to the patient, through a lumen in the catheter 140 that extends the catheter's length. FIG. 22B-22C illustrate example flow measurements 150 recorded by the flow sensing device 144, along with corresponding $CO_2$ concentration measurements 152. FIG. 22B illustrates a situation wherein there is no collateral flow between the target compartment $C_s$ and a neighboring compartment C. FIG. 22C illustrates a situation wherein there is collateral flow between the target compartment $C_s$ and the neighboring compartment C. As illustrated, differences can be seen in both the flow measurements 150 and $CO_2$ concentration measurements 152. Therefore, measurement of various gases can be used to complement flow measurements for data interpretation. The gas composition together with the flow data can also be used to normalize the collateral flow measurement as previously described.

Figure 23A:
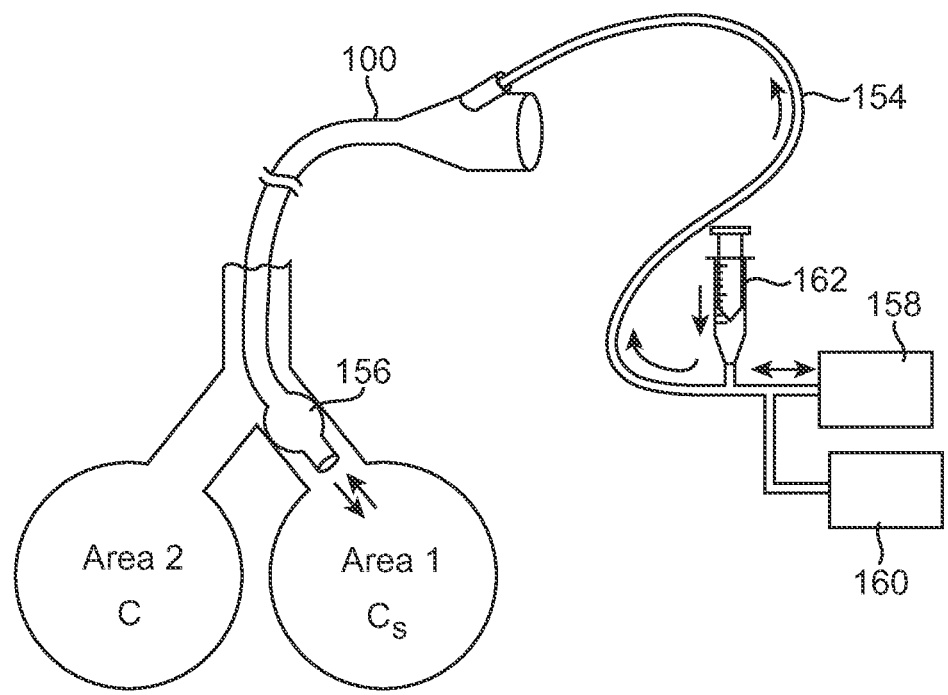
FIGS. 23A-23C illustrate the use of tracer gas to indicate collateral flow.
Figures 23B, 23C:
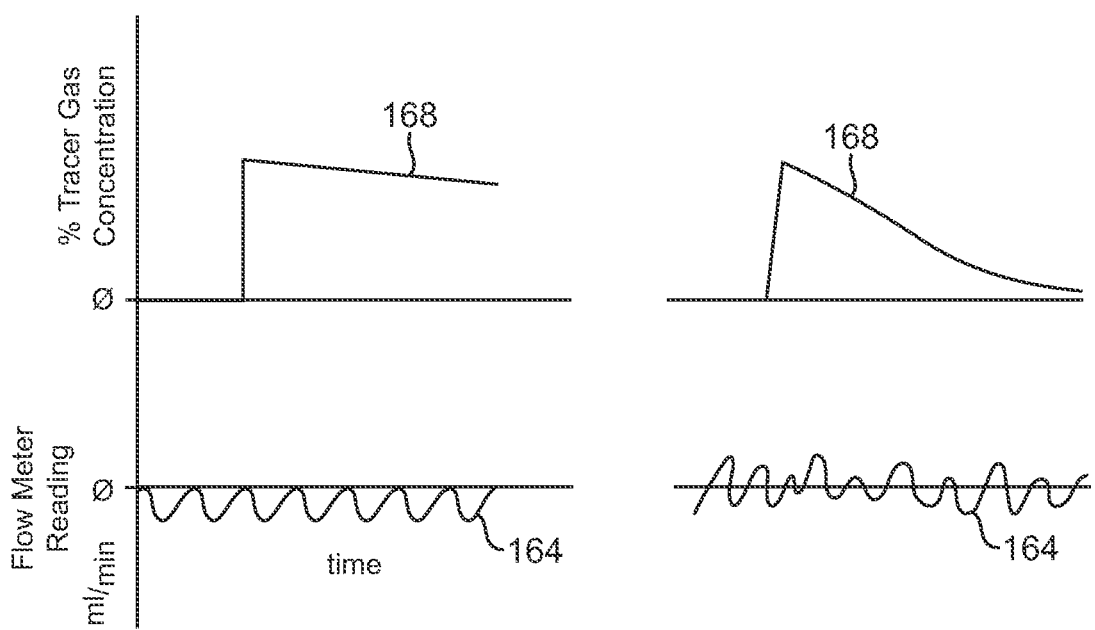

In yet another embodiment of the present invention, tracer gas infusion and measurement may be used to facilitate further interpretation of the airflow data gathered by a flow measuring device. Measurement of the composition of tracer gas, simultaneous with the measurement of airflow as previously described, will facilitate distinguishing between air from a neighboring lung compartment C entering through collateral channels and air that was native to the targeted isolated lung compartment $C_s$. Typically the tracer gas is inert and is not absorbed by the tissue or blood stream in order to eliminate that variable in the collateral flow measurement, however optionally the gas can be a diffusible or absorbable gas for purposes described later. FIG. 23A illustrates a catheter 154 advanced through a bronchoscope 100 having an occlusion member 156 which seals a bronchial lumen leading to a target lumen compartment $C_s$. The catheter 154 is connected with a flow sensing device 158, as described above. In addition, the catheter 154 is connected with a tracer gas sensing device 160 and a tracer gas injection device 162, such as a syringe. Measurements of flow or other respiratory or physiological parameters are then taken, with or without a one-way valve and/or external special container, either at the tip of the catheter 154 in the targeted lung compartment $C_s$ or at the proximal end of the catheter 154, external to the patient, through a lumen in the catheter 154 that extends the catheter's length. FIG. 23B-23C illustrate example flow measurements 164 recorded by the flow sensing device 166, along with corresponding tracer gas concentration measurements 168. FIG. 23B illustrates a situation wherein there is no collateral flow between the target compartment $C_s$ and a neighboring compartment C. As shown, tracer gas concentration remains steady. FIG. 22C illustrates a situation wherein there is collateral flow between the target compartment $C_s$ and the neighboring compartment C. As illustrated, the tracer gas concentration decays due to leakage through collateral channels. The tracer gas decay rate and flow measurements may be compared arithmetically to determine if collateral channels are present and/or the magnitude or size of the channels.

In still another embodiment of the present invention, absorbable gas infusion and measurement may be used to facilitate further interpretation of the airflow data gathered by a flow measuring device. Measurement of the composition of absorbable gas (such as oxygen), simultaneous with the measurement of airflow as previously described, will facilitate distinguishing between air from a neighboring lung compartment C entering through collateral channels and air that was native to the targeted isolated lung compartment $C_s$. FIG. 24A illustrates a catheter 170 advanced through a bronchoscope 100 having an occlusion member 172 which seals a bronchial lumen leading to a target lumen compartment $C_s$. The catheter 170 is connected with a flow sensing device 174, as described above. In addition, the catheter 170 is connected with a gas delivery system 176 and gas source 178. The gas delivery system 176 and flow sensing device 174 are connected with the catheter 170 via a switching valve 180 which allows the flow sensing device 174 to monitor collateral flow after the absorbable gas is delivered. Measurements of flow or other respiratory or physiological parameters are then taken, with or without a one-way valve and/or external special container, either at the tip of the catheter 170 in the targeted lung compartment $C_s$ or at the proximal end of the catheter 170, external to the patient, through a lumen in the catheter 170 that extends the catheter's length. FIG. 23B-23C illustrate example flow measurements 182 recorded by the flow sensing device 174, along with corresponding absorbable concentration measurements 184. FIG. 23B illustrates a situation wherein there is no collateral flow between the target compartment $C_s$ and a neighboring compartment C. As shown, absorbable gas concentration decays via blood diffusion. FIG. 22C illustrates a situation wherein there is collateral flow between the target compartment $C_s$ and the neighboring compartment C. As illustrated, the absorbable gas concentration decays at a faster rate due to diffusion and leakage through collateral channels. The absorbable gas decay rate and flow measurements may be compared arithmetically to determine if collateral channels are present.

Figure 25A:
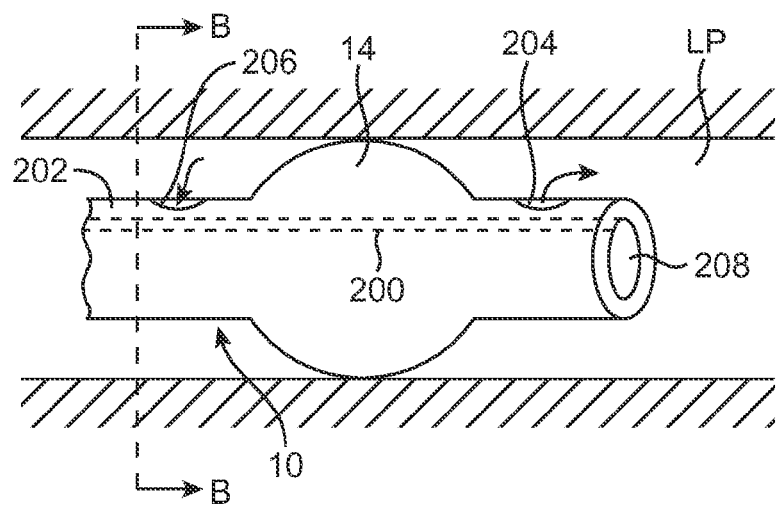
FIGS. 25A-25C illustrate methods and devices for seal testing of an isolation catheter.
Figure 25B:
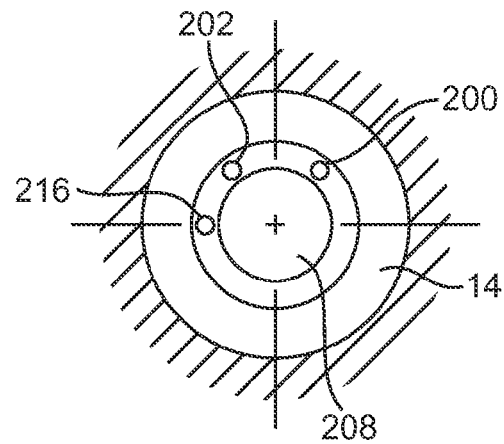
Figure 25C:
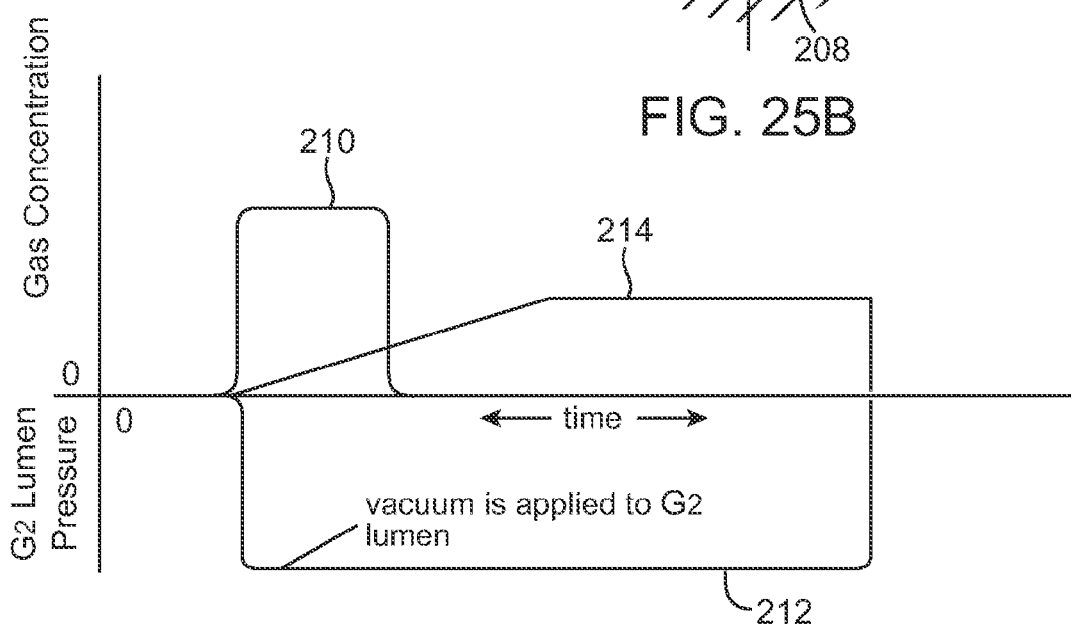

To assist in accuracy of collateral flow measurements and other measurements, devices and methods are provided for seal testing of the isolation catheter. FIG. 25A illustrates a distal end of an isolation catheter 10 having an occlusion member 14 mounted thereon. The occlusion member 14 is shown inflated within a lung passageway LP. It is desired that the occlusion member 14 seals effectively to occlude the passageway LP, otherwise leakage by the occlusion member 14 may, for example, be mistaken for collateral flow thereby introducing error to the collateral flow measurements. Therefore, leak-testing may be performed to ensure appropriate seal. In one embodiment, the isolation catheter 10 includes a gas delivery lumen 200 and a gas sampling lumen 202. The gas delivery lumen 200 exits the catheter 10 distally of the occlusion member 14, such as through a delivery port 204, as illustrated. The gas sampling lumen 202 exits the catheter 10 proximally of the occlusion member 14, such as through sampling port 206. FIG. 25B illustrates a cross-sectional view of FIG. 25A and shows the gas delivery lumen 200 and gas sampling lumen 202 extending through the wall of the catheter 10 while a main lumen 208 extends throughout the length of the catheter 10. An inert gas is introduced through the isolation catheter 10 and is delivered through the delivery port 204. As illustrated in FIG. 25C, concentration of the inert gas within the lung passageway LP (or within a target compartment to which the lung passageway is connected) remains steady immediately after introduction of the gas, as indicated by curve 210. A vacuum is applied to the sampling lumen 202, as indicated by curve 212. In the case of an insufficient seal, gas leakage between the occlusion member 14 and the wall of the lung passageway LP will be suctioned into the sampling lumen 202 and measured, as indicated by curve 214. Such a leak test may be manual, automatic, or semi-automatic. Any processing/control unit external to the body for collateral ventilation testing may include the requisite controls and measuring devices for such leakage measurements.

It may be appreciated that in other embodiments, seal testing may alternatively or in addition be achieved by monitoring pressure within the occlusion member 14. Referring back to FIG. 25B, an inflation lumen 216 is shown extending through the wall of the isolation catheter 10. Typically, the inflation lumen 216 extends to the occlusion member 14 to pass fluid to the occlusion member 14 for inflation. However, in this embodiment the inflation lumen 216 is attached at its proximal end to a pressure gauge to measure pressure within the occlusion member 14. If the measured pressure falls below a desired level for adequate sealing, the pressure may be increased automatically or manually. Such pressure measurements may be taken continuously or semi-continuously.

Figure 26:
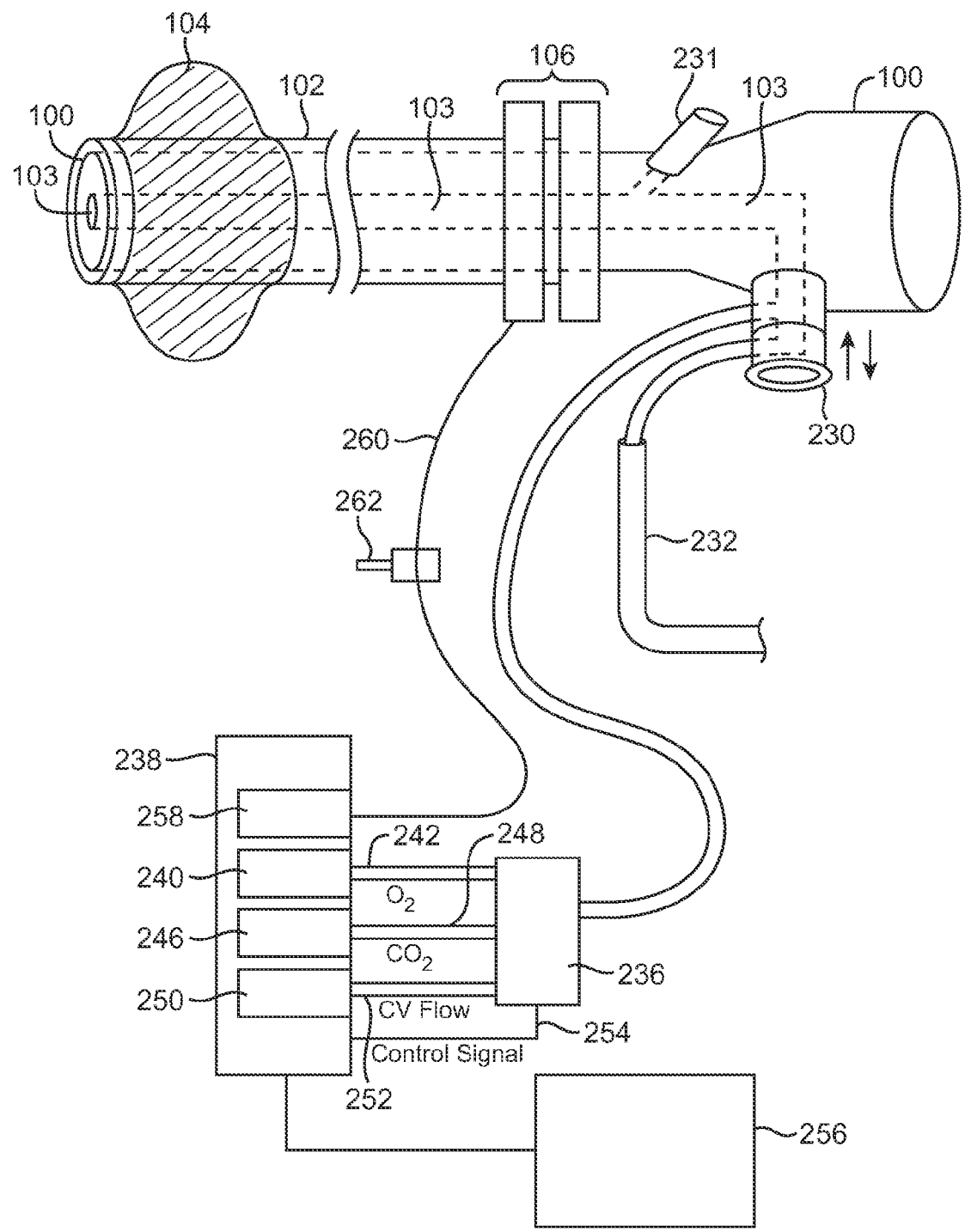
FIG. 26 illustrates an embodiment of a system of the present invention for measuring collateral ventilation in one or more lung passageways.

FIG. 26 illustrates an embodiment of a system of the present invention for measuring collateral ventilation in one or more lung passageways of a patient. Here, the system includes a bronchoscope 100 inserted into an external sheath 102 having an occlusion member 104 and joined at a sheath proximal connector 106. A working channel 103 extends within the bronchoscope 100 to a side port 231 (for introduction of a catheter or other instrument to the working lumen 103) and a connector 230. A suction line 232 connects the working channel 103 with wall suction via the connector 230. In addition, the connector 230 is used to connect the working channel 103 with a control valve 236. The control valve 236 is in turn connected with an electronic unit 238 which includes an electronic control module, a signal acquisition unit and a signal processing unit. In this embodiment, the electronic unit 238 also houses an oxygen delivery compartment 240 containing oxygen for delivery through an oxygen line 242 to the control valve 236 and to the working lumen 103 of the bronchoscope 100. In addition, a carbon dioxide sensor 246 is provided which is connected to a carbon dioxide line 248 which also connects with the control valve 236 and the working lumen 103. Further, a flow meter 250 is connected to a collateral ventilation line 252 which also connects with the control valve 236 and the working lumen 103. The control valve 236 is manipulated by control signals 254 sent from the electronic unit 238. A display 256 is also connected with the electronic unit 238 for visual display of measurement data. In this embodiment, the system also includes a pressure transducer 258 which is connected with the occlusion member 104 via an inflation line 260. The inflation line 250 also includes an inflation port 262 for introducing an inflation fluid to the occlusion member 104. The system of FIG. 26 may be used to perform a variety of the methods, measurements and treatments described herein.

It may be appreciated that any and all possible combinations of the embodiments described herein can be employed. For example, an external special container filled with $O_2$ connected to a targeted compartment via an isolation catheter is included at least by means of using the constituent parts of separate embodiments. Or, for example two of the above embodiments can be combined such that two external special containers are filled with different tracer gases and the special containers connected each to separate isolation catheters that are each isolating neighboring lung areas; analysis of the flow and gas composition in the special containers after a number of breaths may be correlative to collateral ventilation between the areas.

Figure 27:
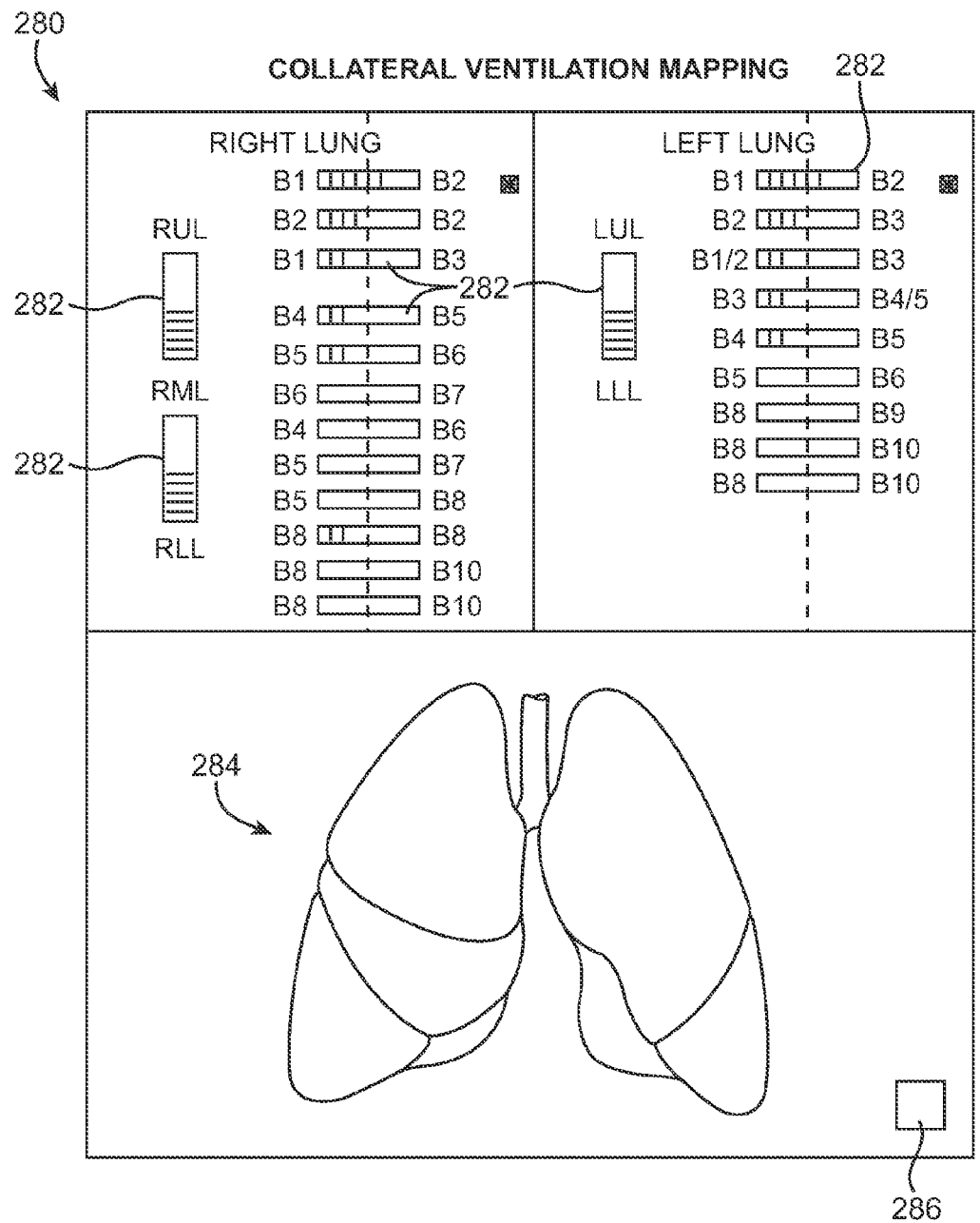
FIG. 27 illustrates an embodiment of a screen indicating collateral ventilation measurements and mapping.

Systems, methods and devices of the present invention may be used to evaluate any number of target compartments $C_s$ within the lungs of a patient. In particular, levels of collateral ventilation may be mapped to the target compartments so that the practitioner may determine the overall condition of the patient and the most desired course of treatment. For example, the right upper lung lobe (RUL) may be isolated and tested for collateral ventilation between it and the neighboring right middle lobe (RML). After the measurement is taken, the isolation catheter may be advanced deeper into the tracheobronchial tree to, for example, the apical segment of the right upper lobe and that segment can be tested for collateral ventilation between it and the neighboring anterior segment and posterior segments. As such, the diagnostic techniques described herein can be used to diagnostically map an area of the lung, or the complete lung with respect to collateral ventilation. FIG. 27 illustrates an embodiment of a screen 280 indicating such measurements and mapping, wherein such a screen 280 may be seen on the display 256 of FIG. 26. Here, the screen 280 shows bar graphs 282 indicating a numerical value of collateral ventilation (or collateral ventilation resistance) between specific lung areas. For example, a bar graph 282 is shown between the RUL and RML indicating the numerical value of collateral ventilation between these two lobes. In addition, bar graphs 282 are shown between individual segments within each lobe. For example, the RUL has target compartments denoted B1, B2, B3, the RML has target compartments denoted B4, B5, B6, and B7, and the right lower lobe (RLL) has target compartments denoted B8, B9, and B10. Likewise, the left upper lobe (LUL) has target compartments denoted B1, B2, B3, B4, B5, and B6, and the left lower lung (LLL) has target compartments denoted B8, B9, B10. A bar graph 282 extending between B1 and B2 within the RUL indicates a numerical value of collateral ventilation (or collateral ventilation resistance) between the specific B1 and B2 target compartments. In addition, the screen 280 includes a visual depiction 284 of at least a portion of the lungs mapping the collateral ventilation data to the appropriate areas of the lungs. For example, the visual depiction 284 may include fissures between the lobes or target compartments wherein the shading of the fissure indicates the completeness of the fissure. In some embodiments, a darker fissure indicates a complete fissure and a lighter fissure indicates an incomplete fissure. Alternatively or in addition, a user may select an area of interest to display a cut-away view of the fissures in the selected area of interest. In addition, the screen 280 may include a link button 286 which changes the screen 280 to another screen 280' depicting measurement data of other variables, such as gas exchange data or other diagnostic measurement data. Thus, the practitioner may use some or all of the visual information provided to assess the condition of the patient and determine the treatment plan.

Figure 28:
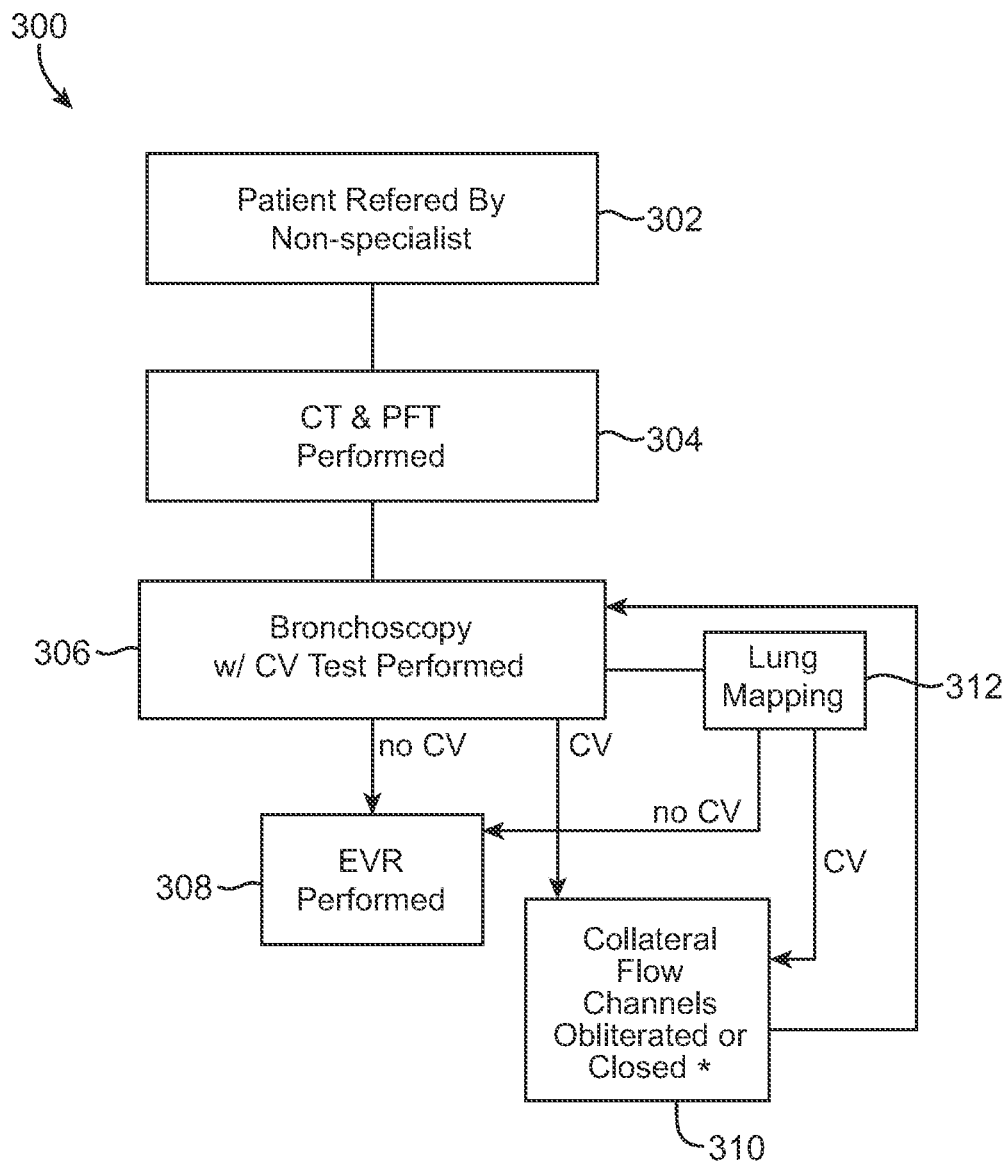
FIG. 28 illustrates an embodiment of a method of treating a patient.

FIG. 28 illustrates an embodiment of a method 300 of treating a patient. In this embodiment, the patient is referred by a non-specialist to a specialist in lung disease and treatment 302. The patient then undergoes computed tomography (CT) 304 to produce detailed images of structures inside the body, particularly the lungs. A CT scanner directs a series of X-ray pulses through the body. Each X-ray pulse lasts only a fraction of a second and represents a "slice" of the organ or area being studied. The slices or pictures are recorded on a computer and can be saved for further study or printed out as photographs. The patient also undergoes pulmonary function testing (PFT) 304. PFT is a breathing test or series of tests to determine, for example, maximum volume of air the lungs can hold, how fast the patient can move air into and out of their lungs, and how easy it is for gas to pass from the lungs to the blood and the surface area available for gas movement. Bronchoscopy with collateral ventilation testing 306 is then performed on the patient. If no collateral ventilation (or a level of collateral ventilation below a threshold) is measured, Endobronchial Volume Reduction (EVR) 308 may be performed on the patient. If collateral ventilation (or a level of collateral ventilation above a threshold) is measured, some or all of the collateral flow channels may be treated 310 (e.g. obliterated or closed), such as with the use of RF, NaCl, sticky substances, perflubron, HF ultrasound, sclerosing agents, heating agents or the like.

Figure 29:
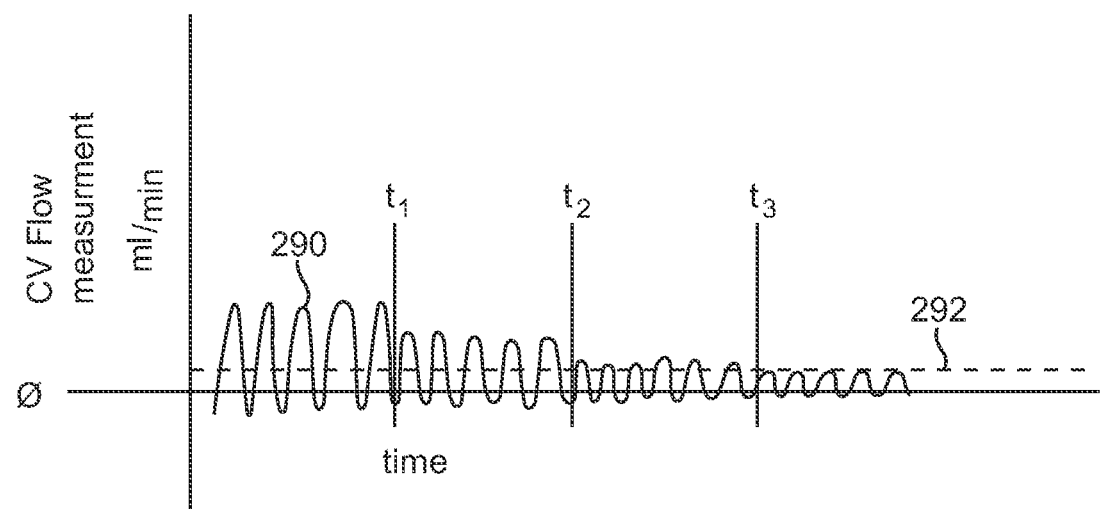
FIG. 29 illustrates an example iterative process of reducing collateral ventilation prior to EVR.

Bronchoscopy with collateral ventilation testing 306 may then be performed again on the patient. If no collateral ventilation (or a level of collateral ventilation below a threshold) is measured, Endobronchial Volume Reduction (EVR) 308 may be performed on the patient. If collateral ventilation (or a level of collateral ventilation above a threshold) is still measured, some or all of the collateral flow channels may be additionally be treated 310. FIG. 29 illustrates an example iterative process of reducing collateral ventilation prior to EVR. An example limit 290 of collateral flow that is desired for successful EVR (i.e. the measurement of collateral flow should be below this level in order to perform EVR) is illustrated. Flow curve 292 prior to $t_1$ shows collateral flow that is above the limit 290. The collateral flow channels are then treated. As shown, the flow curve 292 between $t_1$ and $t_2$ is reduced but still above the limit 290. The collateral flow channels are then further treated. As shown, the flow curve 292 between $t_2$ and $t_3$ is further reduced but still above the limit 290. The collateral flow channels are then further treated. As shown, the flow curve 292 beyond $t_3$ is now below the limit 290 and the patient may be treated with EVR.

Referring back to FIG. 28, in addition to bronchoscopy with collateral ventilation testing 306, lung mapping 312 may be performed. If the lung mapping indicates no collateral ventilation (or a level of collateral ventilation below a threshold), Endobronchial Volume Reduction (EVR) 308 may be performed on the patient. If the lung mapping indicates collateral ventilation (or a level of collateral ventilation above a threshold) is measured, some or all of the collateral flow channels may be treated 310. Such mapping may be repeating after repeated bronchoscopy with collateral ventilation testing 306.

Devices, systems and methods of the present invention may also be useful to assess the sealing or valving performance of any endobronchial prosthesis, such as occlusal stents, plugs, one-way valves or other devices used in endobronchial lung volume reduction procedures. Examples of such devices are described in U.S. Pat. No. 6,287,290, "METHODS, SYSTEMS AND KITS FOR LUNG VOLUME REDUCTION", and U.S. Pat. No. 6,527,761, "METHODS AND DEVICES FOR OBSTRUCTING AND ASPIRATING LUNG TISSUE SEGMENTS", each incorporated herein by reference for all purposes. Devices, systems and methods of the present invention may also be useful to assess the lung for leaks communicating with the pleural space (such as leaks arising from lung volume reduction surgery, other lung surgeries, or spontaneous pneumothorax). In either case, this may be achieved by introducing a catheter to and isolating the lung compartment of interest as previously described and performing the flow measurement as previously described, with or without a check valve. For example in the case of a bronchial occlusal stent, the flow measurement will indicate no inspiratory or expiratory flow if the stent is effectively sealing, but will show flow if the stent is not sealing. One-way valves can be assessed similarly. If the valve is intended to allow expiratory flow but prevent inspiratory flow, the flow measuring device should detect flow during exhalation but not detect flow in the expiratory direction. Should flow be detected during inspiration, the valve may be inadvertently leaking Should no flow be detected in the exhalation direction (assuming the valved area is not atelectatic), the valve may be inadvertently plugged.

Although the foregoing invention has been described in some detail by way of illustration and example, for purposes of clarity of understanding, it will be obvious that various alternatives, modifications and equivalents may be used and the above description should not be taken as limiting in scope of the invention which is defined by the appended claims.

What is claimed is:

1. A method of evaluating a target lung compartment of a patient, the method comprising:
    positioning an instrument within a lung passageway leading to the target lung compartment so that the target lung compartment is isolated;
    injecting an inert gas into the isolated target lung compartment;
    generating at least one measurement of pressure within the target lung segment;
    generating at least one measurement of concentration of inert gas within the target lung segment; and
    analyzing the at least one target lung compartment using a processor with the use of the at least one measurement of pressure and the at least one measurement of concentration of inert gas, wherein analyzing comprises determining a degree of hyperinflation or a state of compliance.

2. A method as in claim 1, further comprising determining a treatment plan at least partially based on the determined degree of hyperinflation.

3. A method as in claim 1, further comprising determining a treatment plan at least partially based on the determined state of compliance.

4. A method as in claim 1, wherein generating the at least one measurement of pressure comprises generating a plurality of measurements of pressure over a predetermined time period.

5. A method as in claim 4, wherein the predetermined time period comprises approximately one minute.

6. A method as in claim 1, wherein generating the at least one measurement of concentration of inert gas comprises generating a plurality of measurements of concentration of inert gas over a predetermined time period.

7. A method as in claim 6, wherein the predetermined time period comprises approximately one minute.

8. A method as in claim 1, wherein the inert gas comprises helium.

9. A method of evaluating a target lung compartment of a patient, the method comprising:
    positioning an instrument within a lung passageway leading to the target lung compartment so that the target lung compartment is isolated;
    injecting an inert gas into the isolated target lung compartment;
    generating at least one measurement of pressure within the target lung segment;
    generating at least one measurement of concentration of inert gas within the target lung segment;
    analyzing the at least one target lung compartment with the use of the at least one measurement of pressure and the at least one measurement of concentration of inert gas, wherein analyzing comprises determining a collateral resistance; and
    determining a treatment plan based on the determined collateral resistance.

10. A system for evaluating a target lung compartment comprising:
    an instrument positionable within a lung passageway leading to the target lung compartment so that the target lung compartment is isolated, wherein the instrument includes a mechanism for injecting an inert gas to the target lung segment;
    at least one sensor which generates measurement data reflecting pressure within the target lung segment;
    at least one sensor which generates measurement data reflecting concentration of an inert gas within the target lung segment; and
    a processor which performs computations with the use of the measurement data reflecting pressure and the measurement data reflecting concentration of inert gas, wherein the computations include calculating a degree of hyperinflation or state of compliance of the target lung compartment.

11. A system as in claim 10, wherein the computations include calculating collateral resistance of the target lung compartment.

12. A system as in claim 10, wherein the measurement data reflecting pressure comprises generating a plurality of measurements of pressure over a predetermined time period.

13. A system as in claim 12, wherein the predetermined time period comprises approximately one minute.

14. A system as in claim 10, wherein the measurement data reflecting concentration of inert gas comprises generating a plurality of measurements of concentration of inert gas over a predetermined time period.

15. A system as in claim 14, wherein the predetermined time period comprises approximately one minute.

16. A system as in claim 10, wherein the inert gas comprises helium.

* * * * *